United States Patent
Fukuda

(10) Patent No.: US 12,150,803 B2
(45) Date of Patent: Nov. 26, 2024

(54) IMAGE PROCESSING DEVICE, RADIOGRAPHY SYSTEM, IMAGE PROCESSING METHOD, AND IMAGE PROCESSING PROGRAM

(71) Applicant: FUJIFILM CORPORATION, Tokyo (JP)

(72) Inventor: Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 376 days.

(21) Appl. No.: 17/694,617

(22) Filed: Mar. 14, 2022

(65) Prior Publication Data
US 2022/0304643 A1  Sep. 29, 2022

(30) Foreign Application Priority Data
Mar. 24, 2021  (JP) .................................. 2021-050390

(51) Int. Cl.
*G01N 15/1434* (2024.01)
*A61B 5/00* (2006.01)
(Continued)

(52) U.S. Cl.
CPC .......... *A61B 6/5205* (2013.01); *A61B 5/0073* (2013.01); *A61B 6/025* (2013.01);
(Continued)

(58) Field of Classification Search
CPC ... G01N 2015/1445; G01N 2021/1787; G01N 2800/7028; G06T 2207/30024;
(Continued)

(56) References Cited

U.S. PATENT DOCUMENTS

| 2012/0051620 A1 | 3/2012 | Fischer et al. |
| 2016/0210741 A1 | 7/2016 | Brendel et al. |
| 2021/0166443 A1 | 6/2021 | Morita |

FOREIGN PATENT DOCUMENTS

| JP | 2016-036671 A | 3/2016 |
| WO | WO-2017188345 A1 * | 11/2017 |

(Continued)

OTHER PUBLICATIONS

Search machine translation of WO 2022/251701 A1 to Zhao, translated Aug. 31, 2024, 292 pages. (Year: 2024).*

(Continued)

*Primary Examiner* — Matthew C Bella
*Assistant Examiner* — Dennis Rosario
(74) *Attorney, Agent, or Firm* — SOLARIS Intellectual Property Group, PLLC

(57) ABSTRACT

A CPU of a console acquires a plurality of projection images, acquires a plurality of tomographic images which are generated using the plurality of projection images and which correspond to each of a plurality of tomographic planes of a breast, performs pseudo-projection at set irradiation positions corresponding to each of the irradiation positions of the plurality of projection images, using a group of tomographic images other than a tomographic image including a reference object image indicating a reference object which is used as a reference for deriving a positional deviation amount between the projection images among the plurality of tomographic images, to generate a plurality of pseudo-projection images without a reference object which do not include the reference object image, and derives the positional deviation amount between the projection images on the basis of component-removed images which include the reference object image and which are obtained by removing components of the plurality of pseudo-projection (Continued)

images without a reference object from the plurality of projection images.

13 Claims, 10 Drawing Sheets

(51) Int. Cl.
*A61B 6/00* (2006.01)
*A61B 6/02* (2006.01)
*G06T 7/00* (2017.01)
*A61B 6/50* (2024.01)
*G01N 21/17* (2006.01)

(52) U.S. Cl.
CPC ............ *G06T 7/0014* (2013.01); *A61B 6/502* (2013.01); *A61B 6/5264* (2013.01); *G01N 2015/1445* (2013.01); *G01N 2021/1787* (2013.01); *G06T 2207/10072* (2013.01); *G06T 2207/10112* (2013.01); *G06T 2207/30068* (2013.01)

(58) Field of Classification Search
CPC ......... G06T 2207/30068; G06T 7/0012; G06T 2211/421; G06T 2211/40; G06T 2207/10072; G06T 2207/10112; G06T 5/70; G06T 7/0014; G06T 7/0002; G06T 2207/30096; G06T 11/003; G06T 11/005; G06T 11/008; G06T 11/006; G06T 7/11; G06T 7/194; G06T 2207/10081; G06T 2207/10076; G06T 2207/10084; Y10S 378/901; A61B 6/032; A61B 6/025; A61B 6/502; A61B 5/0073; A61B 5/0091; A61B 6/5258; A61B 6/5264; A61B 6/527

See application file for complete search history.

(56) References Cited

FOREIGN PATENT DOCUMENTS

| | | | |
|---|---|---|---|
| WO | 2020/067475 A1 | 4/2020 | |
| WO | WO-2022251701 A1 * | 12/2022 | ............... A61B 6/00 |

OTHER PUBLICATIONS

Search machine translation of WO 2017/188345 A1 to Haga, translated Aug. 31, 2024, 15 pages. (Year: 2024).*

English language translation of the following: Office action dated Jul. 30, 2024 from the JPO in a Japanese patent application No. 2021-050390 corresponding to the instant patent application. This office action translation is submitted now in order to supplement the understanding of the cited references which are being disclosed in the instant Information Disclosure Statement.

* cited by examiner

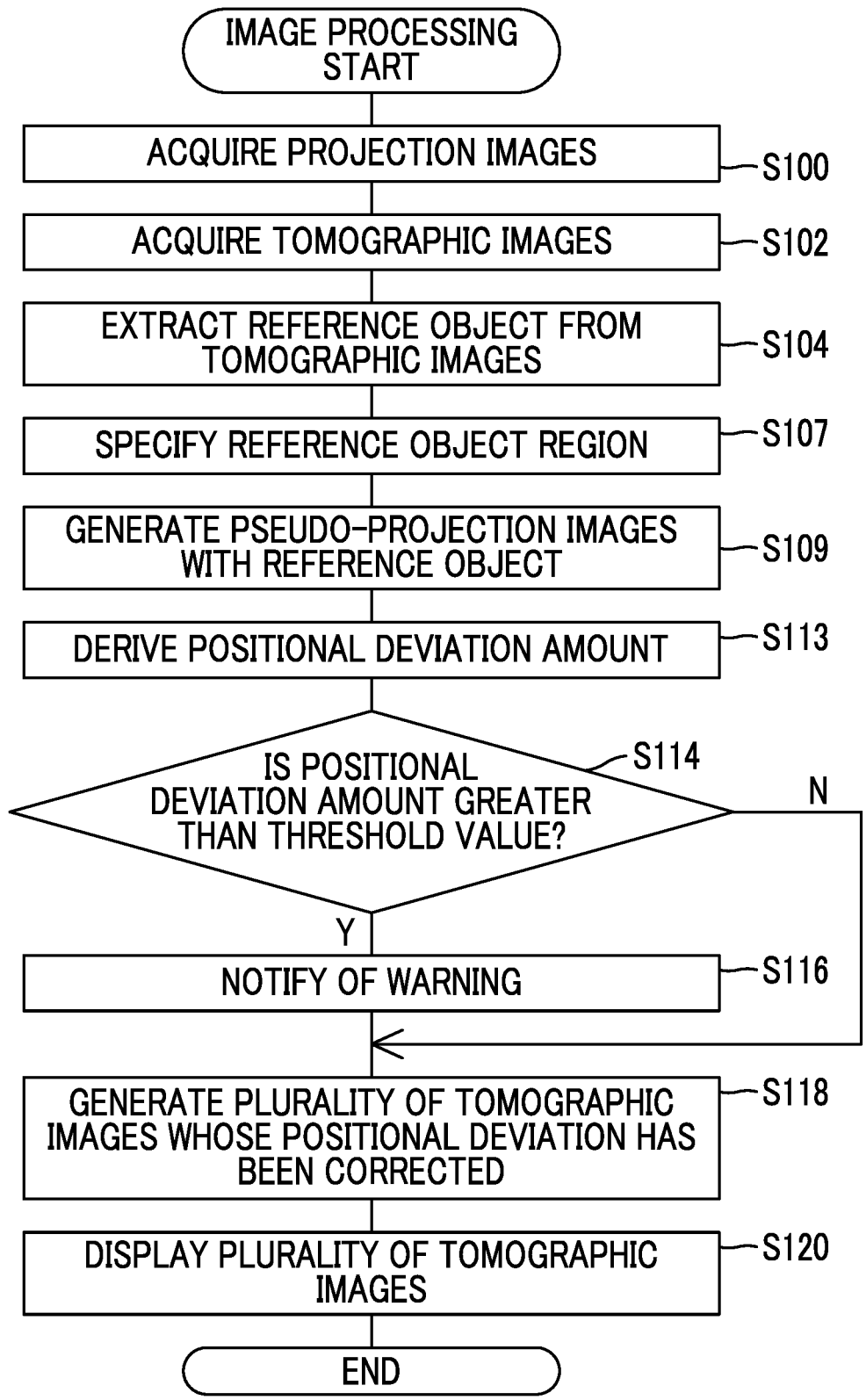

IMAGE PROCESSING DEVICE, RADIOGRAPHY SYSTEM, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2021-050390 filed on Mar. 24, 2021. The above application is hereby expressly incorporated by reference, in its entirety, into the present application.

BACKGROUND

1. Technical Field

The present disclosure relates to an image processing device, a radiography system, an image processing method, and an image processing program.

2. Description of the Related Art

In general, so-called tomosynthesis imaging is known which irradiates an object with radiation emitted from a radiation source at each of a plurality of irradiation positions having different irradiation angles to capture a plurality of projection images of the object at different irradiation positions.

In the tomosynthesis imaging, since a plurality of projection images are captured, positional deviation between the projection images is likely to occur because of the influence of, for example, the movement of an object or the positional deviation of a radiation source at each irradiation position. There is a problem in that tomographic images generated using a plurality of projection images having a positional deviation therebetween are blurred images.

Therefore, a technique which corrects the positional deviation between the projection images is known. For example, WO2020/067475A discloses a technique which derives a positional deviation amount between a plurality of projection images on the basis of a feature point in a tomographic plane corresponding to a tomographic image in which the feature point has been detected.

SUMMARY

However, the projection image has structures arranged in a direction in which radiation is emitted and includes a large amount of information. Therefore, in many cases, the projection image includes information of the image of a structure that is an obstacle to deriving the positional deviation amount between the projection images. In the technique according to the related art, the accuracy of deriving the positional deviation amount between the projection images is likely to be reduced because of the influence of unnecessary information.

The present disclosure has been made in view of the above circumstances, and an object of the present disclosure is to provide an image processing device, a radiography system, an image processing method, and an image processing program that can derive a positional deviation amount between projection images with high accuracy.

In order to achieve the above object, according to a first aspect of the present disclosure, there is provided an image processing device that processes a plurality of projection images obtained by irradiating an object with radiation emitted from a radiation source at each of a plurality of irradiation positions having different irradiation angles. The image processing device comprises at least one processor. The processor acquires the plurality of projection images, acquires a plurality of tomographic images which are generated using the plurality of projection images and which correspond to each of a plurality of tomographic planes of the object, performs pseudo-projection at set irradiation positions corresponding to each of the irradiation positions of the plurality of projection images, using a group of second tomographic images other than a first tomographic image including a reference object image indicating a reference object which is used as a reference for deriving a positional deviation amount between the projection images among the plurality of tomographic images, to generate a plurality of pseudo-projection images without a reference object which do not include the reference object image, and derives the positional deviation amount between the projection images on the basis of component-removed images which include the reference object image and which are obtained by removing components of the plurality of pseudo-projection images without a reference object from the plurality of projection images.

According to a second aspect of the present disclosure, in the image processing device according to the first aspect, the processor may derive the positional deviation amount on the basis of the component-removed images and the first tomographic image.

According to a third aspect of the present disclosure, in the image processing device according to the first aspect or the second aspect, the processor may generate, as the pseudo-projection image without a reference object, a partial pseudo-projection image obtained by performing the pseudo-projection on a partial region of the group of second tomographic images which corresponds to a reference object region that is a portion including the reference object image in the first tomographic image, and may remove a component of the partial pseudo-projection image from a partial image of the projection image which corresponds to the partial pseudo-projection image to generate the component-removed image.

According to a fourth aspect of the present disclosure, in the image processing device according to any one of the first to third aspects, the processor may generate images indicating differences between the plurality of projection images and the plurality of pseudo-projection images without a reference object as the component-removed images.

According to a fifth aspect of the present disclosure, in the image processing device according to any one of the first to third aspects, the processor may subtract a pixel value of the pseudo-projection image without a reference object from a pixel value of the projection image for each corresponding pixel to generate the component-removed image.

According to a sixth aspect of the present disclosure, in the image processing device according to any one of the first to third aspects, the processor may reduce a pixel value of a pixel, which is correlated with the pseudo-projection image without a reference object, in the projection image to generate the component-removed image.

In order to achieve the above object, according to a seventh aspect of the present disclosure, there is provided an image processing device that processes a plurality of projection images obtained by irradiating an object with radiation emitted from a radiation source at each of a plurality of irradiation positions having different irradiation angles. The image processing device comprises at least one processor.

The processor acquires the plurality of projection images, acquires a plurality of tomographic images which are generated using the plurality of projection images and which correspond to each of a plurality of tomographic planes of the object, performs pseudo-projection at set irradiation positions corresponding to each of the irradiation positions of the plurality of projection images, using a tomographic image including a reference object image indicating a reference object which is used as a reference for deriving a positional deviation amount between the projection images among the plurality of tomographic images, to generate a plurality of pseudo-projection images with a reference object which include the reference object image, and derives the positional deviation amount between the projection images on the basis of the plurality of projection images and the plurality of pseudo-projection images with a reference object.

According to an eighth aspect of the present disclosure, in the image processing device according to the seventh aspect, the processor may generate the pseudo-projection image with a reference object using only the tomographic image including the reference object.

According to a ninth aspect of the present disclosure, in the image processing device according to the seventh aspect or the eighth aspect, the processor may generate, as the pseudo-projection image with a reference object, a partial pseudo-projection image obtained by performing the pseudo-projection on a reference object region including the reference object image in the tomographic image.

According to a tenth aspect of the present disclosure, in the image processing device according to any one of the first to ninth aspects, the processor may further generate a plurality of tomographic images in each of the plurality of tomographic planes on the basis of the plurality of projection images and the positional deviation amount.

According to an eleventh aspect of the present disclosure, in the image processing device according to any one of the first to tenth aspects, in a case in which the positional deviation amount is greater than a predetermined threshold value, the processor may perform notification.

According to a twelfth aspect of the present disclosure, in the image processing device according to any one of the first to eleventh aspects, the processor may perform the pseudo-projection on each of a plurality of reference objects using second tomographic images.

According to a thirteenth aspect of the present disclosure, in the image processing device according to any one of the first to eleventh aspects, the object may be a breast, and the reference object may be a calcification or a mammary gland.

Furthermore, in order to achieve the above object, according to a fourteenth aspect of the present disclosure, there is provided a radiography system comprising: a radiation source that generates radiation; a radiography apparatus that performs tomosynthesis imaging which irradiates an object with the radiation emitted from the radiation source at each of a plurality of irradiation positions having different irradiation angles to capture projection images of the object at each of the irradiation positions; and the image processing device according to the present disclosure.

Moreover, in order to achieve the above object, according to a fifteenth aspect of the present disclosure, there is provided an image processing method that is executed by a computer and that processes a plurality of projection images obtained by irradiating an object with radiation emitted from a radiation source at each of a plurality of irradiation positions having different irradiation angles. The image processing method comprises: acquiring the plurality of projection images; acquiring a plurality of tomographic images which are generated using the plurality of projection images and which correspond to each of a plurality of tomographic planes of the object; performing pseudo-projection at set irradiation positions corresponding to each of the irradiation positions of the plurality of projection images, using a group of second tomographic images other than a first tomographic image including a reference object image indicating a reference object which is used as a reference for deriving a positional deviation amount between the projection images among the plurality of tomographic images, to generate a plurality of pseudo-projection images without a reference object which do not include the reference object image; and deriving the positional deviation amount between the projection images on the basis of component-removed images which include the reference object image and which are obtained by removing components of the plurality of pseudo-projection images without a reference object from the plurality of projection images.

In addition, in order to achieve the above object, according to a sixteenth aspect of the present disclosure, there is provided an image processing method that is executed by a computer and that processes a plurality of projection images obtained by irradiating an object with radiation emitted from a radiation source at each of a plurality of irradiation positions having different irradiation angles. The image processing method comprises: acquiring the plurality of projection images; acquiring a plurality of tomographic images which are generated using the plurality of projection images and which correspond to each of a plurality of tomographic planes of the object; performing pseudo-projection at set irradiation positions corresponding to each of the irradiation positions of the plurality of projection images, using a tomographic image including a reference object image indicating a reference object which is used as a reference for deriving a positional deviation amount between the projection images among the plurality of tomographic images, to generate a plurality of pseudo-projection images with a reference object which include the reference object image; and deriving the positional deviation amount between the projection images on the basis of the plurality of projection images and the plurality of pseudo-projection images with a reference object.

Further, in order to achieve the above object, according to a seventeenth aspect of the present disclosure, there is provided an image processing program that processes a plurality of projection images obtained by irradiating an object with radiation emitted from a radiation source at each of a plurality of irradiation positions having different irradiation angles. The image processing program causes a computer to perform a process comprising: acquiring the plurality of projection images; acquiring a plurality of tomographic images which are generated using the plurality of projection images and which correspond to each of a plurality of tomographic planes of the object; performing pseudo-projection at set irradiation positions corresponding to each of the irradiation positions of the plurality of projection images, using a group of second tomographic images other than a first tomographic image including a reference object image indicating a reference object which is used as a reference for deriving a positional deviation amount between the projection images among the plurality of tomographic images, to generate a plurality of pseudo-projection images without a reference object which do not include the reference object image; and deriving the positional deviation amount between the projection images on the basis of component-removed images which include the reference object image and which are obtained by removing components of the plurality of pseudo-projection images without a reference object from the plurality of projection images.

Furthermore, in order to achieve the above object, according to an eighteenth aspect of the present disclosure, there is provided an image processing program that processes a plurality of projection images obtained by irradiating an object with radiation emitted from a radiation source at each of a plurality of irradiation positions having different irradiation angles. The image processing program causes a computer to perform a process comprising: acquiring the plurality of projection images; acquiring a plurality of tomographic images which are generated using the plurality of projection images and which correspond to each of a plurality of tomographic planes of the object; performing pseudo-projection at set irradiation positions corresponding to each of the irradiation positions of the plurality of projection images, using a tomographic image including a reference object image indicating a reference object which is used as a reference for deriving a positional deviation amount between the projection images among the plurality of tomographic images, to generate a plurality of pseudo-projection images with a reference object which include the reference object image; and deriving the positional deviation amount between the projection images on the basis of the plurality of projection images and the plurality of pseudo-projection images with a reference object.

According to the present disclosure, it is possible to derive the positional deviation amount between the projection images with high accuracy.

BRIEF DESCRIPTION OF THE DRAWINGS

Exemplary embodiments according to the technique of the present disclosure will be described in detail based on the following figures, wherein:

FIG. 13 is a flowchart illustrating an example of the flow of image processing by the console according to the second embodiment.

DETAILED DESCRIPTION

Hereinafter, an embodiment of the present disclosure will be described in detail with reference to the drawings. In addition, this embodiment does not limit the present disclosure.

First Embodiment

Figure 1:
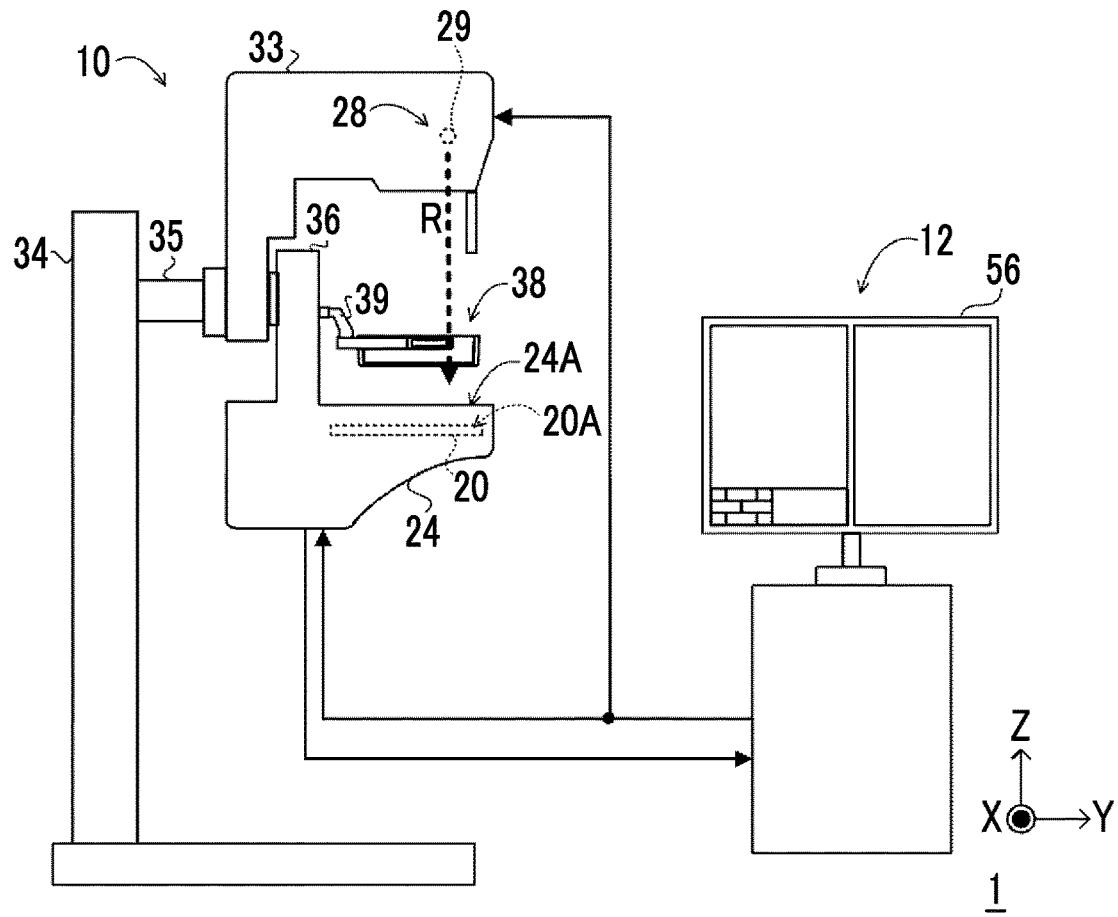
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12.

First, the mammography apparatus 10 according to this embodiment will be described. FIG. 1 is a side view illustrating an example of the outward appearance of the mammography apparatus 10 according to this embodiment. In addition, FIG. 1 illustrates an example of the outward appearance of the mammography apparatus 10 as viewed from a left side of a subject.

The mammography apparatus 10 according to this embodiment is an apparatus that is operated under the control of the console 12 and that irradiates a breast of the subject as an object with radiation R (for example, X-rays) to capture a radiographic image of the breast. In addition, the mammography apparatus 10 may be an apparatus that images the breast of the subject not only in a state in which the subject is standing (standing state) but also in a state in which the subject is sitting on, for example, a chair (including a wheelchair) (sitting state).

Furthermore, the mammography apparatus 10 according to this embodiment has a function of performing normal imaging that captures images at an irradiation position where a radiation source 29 is disposed along a normal direction to a detection surface 20A of a radiation detector 20 and so-called tomosynthesis imaging that captures images while moving the radiation source 29 to each of a plurality of irradiation positions.

The radiation detector 20 detects the radiation R transmitted through the breast which is the object. Specifically, the radiation detector 20 detects the radiation R that has entered the breast of the subject and an imaging table 24 and that has reached the detection surface 20A of the radiation detector 20, generates a radiographic image on the basis of the detected radiation R, and outputs image data indicating the generated radiographic image. In the following description, in some cases, a series of operations of emitting the radiation R from the radiation source 29 and generating a radiographic image using the radiation detector 20 is referred to as "imaging". The type of the radiation detector 20 according to this embodiment is not particularly limited. For example, the radiation detector 20 may be an indirect-conversion-type radiation detector that converts the radiation R into light and converts the converted light into charge or a direct-conversion-type radiation detector that directly converts the radiation R into charge.

As illustrated in FIG. 1, the radiation detector 20 is disposed in the imaging table 24. In the mammography apparatus 10 according to this embodiment, in a case in which imaging is performed, the breast of the subject is positioned on an imaging surface 24A of the imaging table 24 by a user.

A compression plate 38 that is used to compress the breast in a case in which imaging is performed is attached to a compression unit 36 that is provided in the imaging table 24. Specifically, the compression unit 36 is provided with a compression plate driving unit (not illustrated) that moves the compression plate 38 in a direction (hereinafter, referred to as an "up-down direction") toward or away from the imaging table 24. A support portion 39 of the compression plate 38 is detachably attached to the compression plate driving unit and is moved in the up-down direction by the compression plate driving unit to compress the breast of the subject between the compression plate 38 and the imaging table 24. The compression plate 38 according to this embodiment is an example of a compression member according to the present disclosure.

As illustrated in FIG. 1, the mammography apparatus 10 according to this embodiment comprises the imaging table 24, an arm portion 33, a base 34, and a shaft portion 35. The arm portion 33 is held by the base 34 so as to be movable in the up-down direction (Z-axis direction). In addition, the arm portion 33 can be rotated with respect to the base 34 by the shaft portion 35. The shaft portion 35 is fixed to the base 34, and the shaft portion 35 and the arm portion 33 are rotated integrally.

Gears are provided in each of the shaft portion 35 and the compression unit 36 of the imaging table 24. The gears can be switched between an engaged state and a non-engaged state to switch between a state in which the compression unit 36 of the imaging table 24 and the shaft portion 35 are connected and rotated integrally and a state in which the shaft portion 35 is separated from the imaging table 24 and runs idle. In addition, components for switching between transmission and non-transmission of power of the shaft portion 35 are not limited to the gears, and various mechanical elements may be used.

Each of the arm portion 33 and the imaging table 24 can be relatively rotated with respect to the base 34, using the shaft portion 35 as a rotation axis. In this embodiment, engagement portions (not illustrated) are provided in each of the base 34, the arm portion 33, and the compression unit 36 of the imaging table 24. The state of the engagement portions is switched to connect each of the arm portion 33 and the compression unit 36 of the imaging table 24 to the base 34. One or both of the arm portion 33 and the imaging table 24 connected to the shaft portion 35 are integrally rotated on the shaft portion 35.

Figure 2:
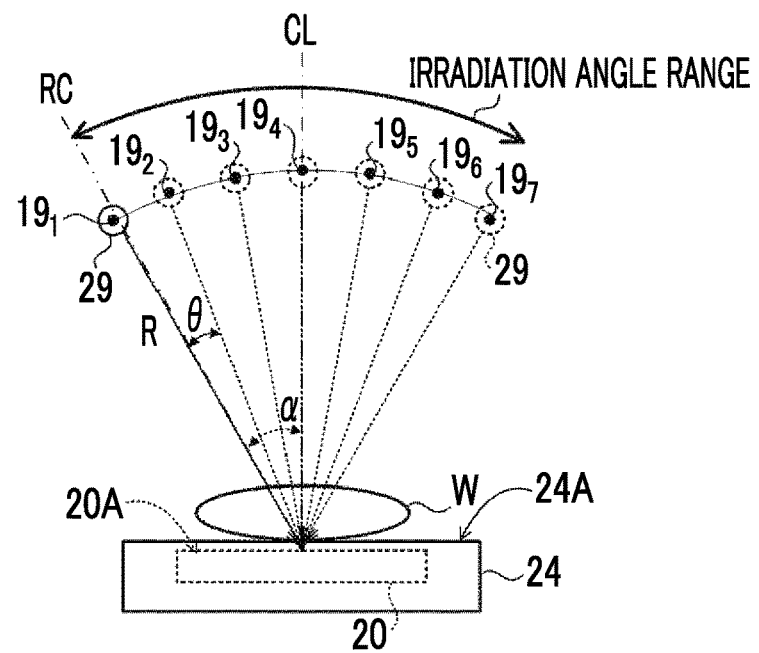
FIG. 2 is a diagram illustrating an example of tomosynthesis imaging.

In a case in which the mammography apparatus 10 performs the tomosynthesis imaging, the radiation source 29 of a radiation emitting unit 28 is sequentially moved to each of the plurality of irradiation positions having different irradiation angles by the rotation of the arm portion 33. The radiation source 29 includes a radiation tube (not illustrated) that generates the radiation R, and the radiation tube is moved to each of the plurality of irradiation positions according to the movement of the radiation source 29. FIG. 2 is a diagram illustrating an example of the tomosynthesis imaging. In addition, the compression plate 38 is not illustrated in FIG. 2. In this embodiment, as illustrated in FIG. 2, the radiation source 29 is moved to irradiation positions $19_k$ ($k=1, 2, \ldots$; the maximum value is 7 in FIG. 2) with different irradiation angles which are arranged at an interval of a predetermined angle θ, that is, positions where the radiation R is emitted to the detection surface 20A of the radiation detector 20 at different angles. At each of the irradiation positions $19_k$, the radiation source 29 emits the radiation R to a breast W in response to an instruction from the console 12, and the radiation detector 20 captures a radiographic image. In the radiography system 1, in a case in which the tomosynthesis imaging that moves the radiation source 29 to each of the irradiation positions $19_k$ and that captures radiographic images at each of the irradiation positions $19_k$ is performed, seven radiographic images are obtained in the example illustrated in FIG. 2. In addition, in the following description, in the tomosynthesis imaging, in a case in which a radiographic image captured at each irradiation position 19 is distinguished from other radiographic images, it is referred to as a "projection image". Further, in a case in which a radiographic image is generically referred to regardless of the type, such as a projection image and a tomographic image which will be described below, it is simply referred to as a "radiographic image". Furthermore, in the following description, in a case in which the irradiation positions $19_k$ are generically referred to, a reference letter k for distinguishing each irradiation position is omitted, and the irradiation positions $19_k$ are referred to as "irradiation positions 19". Further, in the following description, for the image corresponding to the irradiation position $19_k$, such as the projection image captured at each irradiation position $19_k$, the reference letter k indicating the irradiation position $19_k$ is given to the reference numeral indicating each image.

In addition, as illustrated in FIG. 2, the irradiation angle of the radiation R means an angle α formed between a normal line CL to the detection surface 20A of the radiation detector 20 and a radiation axis RC. The radiation axis RC means an axis that connects the focus of the radiation source 29 at each irradiation position 19 and a preset position such as the center of the detection surface 20A. Further, here, it is assumed that the detection surface 20A of the radiation detector 20 is substantially parallel to the imaging surface 24A. Hereinafter, a predetermined range in which the irradiation angles are different in the tomosynthesis imaging as illustrated in FIG. 2 is referred to as an "irradiation angle range".

On the other hand, in a case in which the mammography apparatus 10 performs the normal imaging, the radiation source 29 of the radiation emitting unit 28 remains at the irradiation position $19_k$ (the irradiation position $19_k$ along the normal direction, the irradiation position $19_4$ in FIG. 2) where the irradiation angle α is 0 degrees. The radiation source 29 emits the radiation R in response to an instruction from the console 12, and the radiation detector 20 captures a radiographic image.

Figure 3:
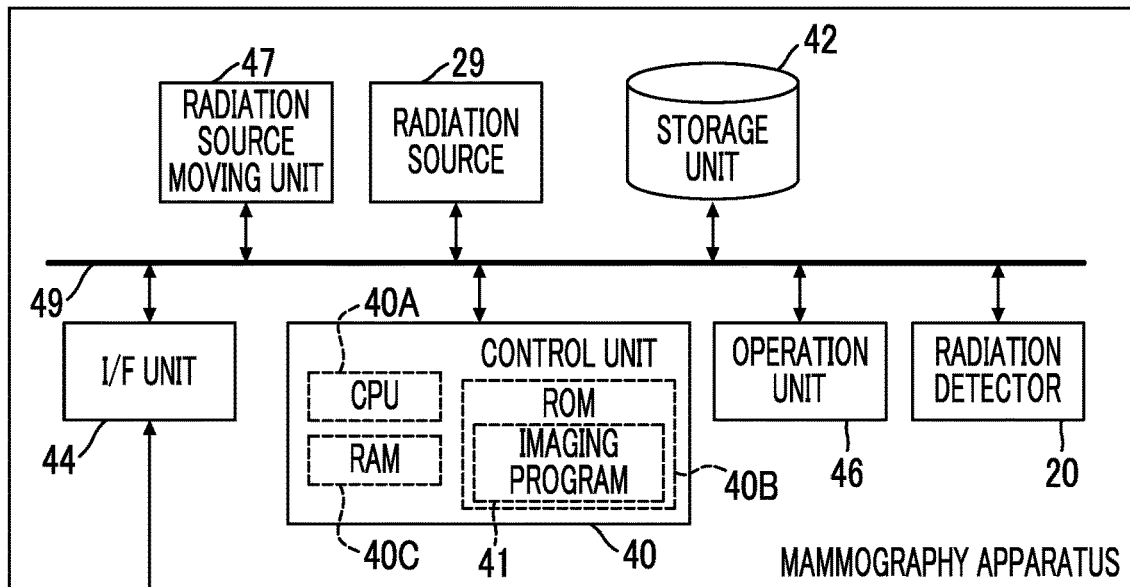
FIG. 3 is a block diagram illustrating an example of the configuration of a mammography apparatus and a console according to a first embodiment.

Further, FIG. 3 is a block diagram illustrating an example of the configuration of the mammography apparatus 10 and the console 12 according to this embodiment. As illustrated in FIG. 3, the mammography apparatus 10 according to this embodiment further comprises a control unit 40, a storage unit 42, an interface (I/F) unit 44, an operation unit 46, and a radiation source moving unit 47. The control unit 40, the storage unit 42, the I/F unit 44, the operation unit 46, and the radiation source moving unit 47 are connected to each other through a bus 49, such as a system bus or a control bus, such that they can transmit and receive various kinds of information.

The control unit 40 controls the overall operation of the mammography apparatus 10 under the control of the console 12. The control unit 40 comprises a central processing unit (CPU) 40A, a read only memory (ROM) 40B, and a random access memory (RAM) 40C. For example, various programs including an imaging program 41 which is executed by the CPU 40A and which performs control related to the capture of a radiographic image are stored in the ROM 40B in advance. The RAM 40C temporarily stores various kinds of data.

For example, the image data of the radiographic image captured by the radiation detector 20 and various other kinds of information are stored in the storage unit 42. A specific example of the storage unit 42 is a hard disk drive (HDD), a solid state drive (SSD), or the like. The I/F unit 44 transmits and receives various kinds of information to and from the console 12 using wireless communication or wired communication. The image data of the radiographic image captured by the radiation detector 20 in the mammography apparatus 10 is transmitted to the console 12 through the I/F unit 44 by wireless communication or wired communication.

Each of the control unit 40, the storage unit 42, and the I/F unit 44 according to this embodiment is provided in the imaging table 24.

In addition, the operation unit 46 is provided as a plurality of switches in, for example, the imaging table 24 of the mammography apparatus 10. Further, the operation unit 46 may be provided as a touch panel switch or may be provided as a foot switch that is operated by the feet of the user such as a doctor or a radiology technician.

The radiation source moving unit 47 has a function of moving the radiation source 29 to each of the plurality of irradiation positions 19 under the control of the control unit 40 in a case in which the tomosynthesis imaging is performed as described above. Specifically, the radiation source moving unit 47 rotates the arm portion 33 with respect to the imaging table 24 to move the radiation source 29 to each of the plurality of irradiation positions 19. The radiation source moving unit 47 according to this embodiment is provided inside the arm portion 33.

On the other hand, the console 12 according to this embodiment has a function of controlling the mammography apparatus 10 using, for example, an imaging order and various kinds of information acquired from a radiology information system (RIS) through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. Various programs which are executed by the CPU 50A and which include an image generation program 51 are stored in the ROM 50B in advance. The RAM 50C temporarily stores various kinds of data. In this embodiment, the CPU 50A is an example of a processor according to the present disclosure, and the console 12 is an example of an image processing device according to the present disclosure. In addition, the image generation program 51 according to this embodiment is an example of an image processing program according to the present disclosure.

For example, the image data of the radiographic image captured by the mammography apparatus 10 and various other kinds of information are stored in the storage unit 52. A specific example of the storage unit 52 is an HDD, an SSD, or the like.

The operation unit 56 is used by the user to input, for example, instructions which are related to the capture of a radiographic image and which include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS, and a picture archiving and communication system (PACS) using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
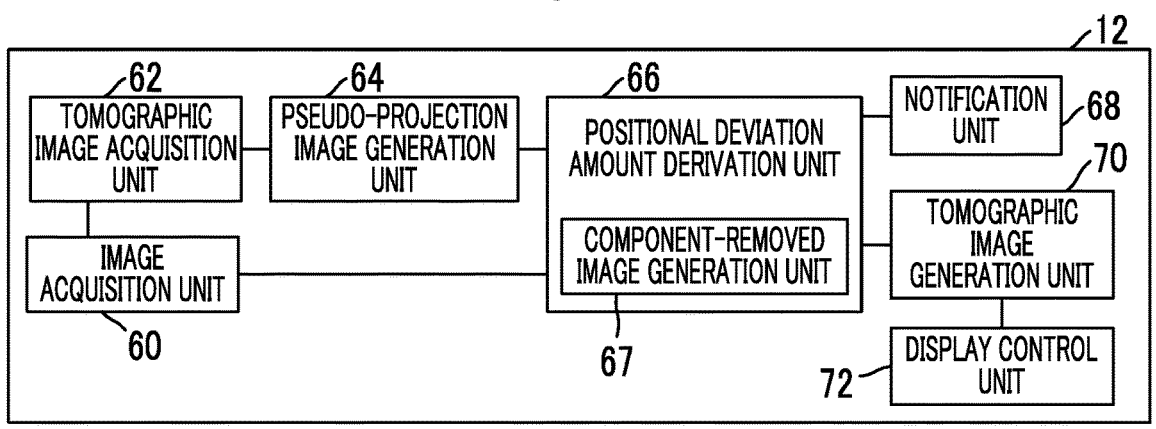
FIG. 4 is a functional block diagram illustrating an example of the functions of the console according to the first embodiment.

The console 12 according to this embodiment has a function of correcting the positional deviation between a plurality of projection images obtained by the tomosynthesis imaging. FIG. 4 is a functional block diagram illustrating an example of a configuration related to the function of correcting the positional deviation between the plurality of projection images obtained by the tomosynthesis imaging in the console 12 according to this embodiment. As illustrated in FIG. 4, the console 12 comprises an image acquisition unit 60, a tomographic image acquisition unit 62, a pseudo-projection image generation unit 64, a positional deviation amount derivation unit 66, a notification unit 68, a tomographic image generation unit 70, and a display control unit 72. For example, in the console 12 according to this embodiment, the CPU 50A of the control unit 50 executes the image generation program 51 stored in the ROM 50B to function as the image acquisition unit 60, the tomographic image acquisition unit 62, the pseudo-projection image generation unit 64, the positional deviation amount derivation unit 66, the notification unit 68, the tomographic image generation unit 70, and the display control unit 72.

The image acquisition unit 60 has a function of acquiring a plurality of projection images. Specifically, the image acquisition unit 60 according to this embodiment acquires image data indicating a plurality of projection images obtained by the tomosynthesis imaging in the mammography apparatus 10. The image acquisition unit 60 outputs the acquired image data indicating the plurality of projection images to the tomographic image acquisition unit 62 and the positional deviation amount derivation unit 66.

The tomographic image acquisition unit 62 has a function of acquiring a plurality of tomographic images corresponding to each of a plurality of tomographic planes of the breast as the object. Specifically, the tomographic image acquisition unit 62 according to this embodiment generates a plurality of tomographic images corresponding to each of the plurality of tomographic planes of the breast, using the plurality of projection images acquired by the image acquisition unit 60, and acquires the plurality of tomographic images.

In addition, a method by which the tomographic image acquisition unit 62 generates the plurality of tomographic images is not particularly limited, and a known method may be used. For example, reconstruction may be performed by a back projection method, such as a filter back projection (FBP) method or an iterative reconstruction method, or a known technique may be applied. Further, the tomographic planes of the plurality of tomographic images generated by the tomographic image acquisition unit 62 are substantially parallel to the detection surface 20A of the radiation detector 20 and are substantially parallel to the imaging surface 24A of the imaging table 24. The position of the tomographic planes of the plurality of tomographic images generated by the tomographic image acquisition unit 62, that is, the height of the tomographic planes from the imaging surface 24A of the imaging table 24, is not particularly limited. Specifically, the height of the tomographic plane can be determined according to, for example, the size of a region of interest, the quality of the radiographic image, the processing load of arithmetic processing in the generation of the tomographic image, and an instruction from the user. The tomographic image acquisition unit 62 outputs image data indicating the acquired plurality of tomographic images to the pseudo-projection image generation unit 64.

The pseudo-projection image generation unit 64 has a function of performing pseudo-projection at set irradiation positions corresponding to the irradiation positions of each of the plurality of projection images, using a group of tomographic images other than a tomographic image including a reference object which is used as a reference for deriving the positional deviation amount between the projection images among the plurality of tomographic images, to generate a plurality of pseudo-projection images that do not include a reference object image indicating the reference object. In this embodiment, the pseudo-projection image that does not include the reference object image is referred to as a "pseudo-projection image without a reference object".

Figure 5:
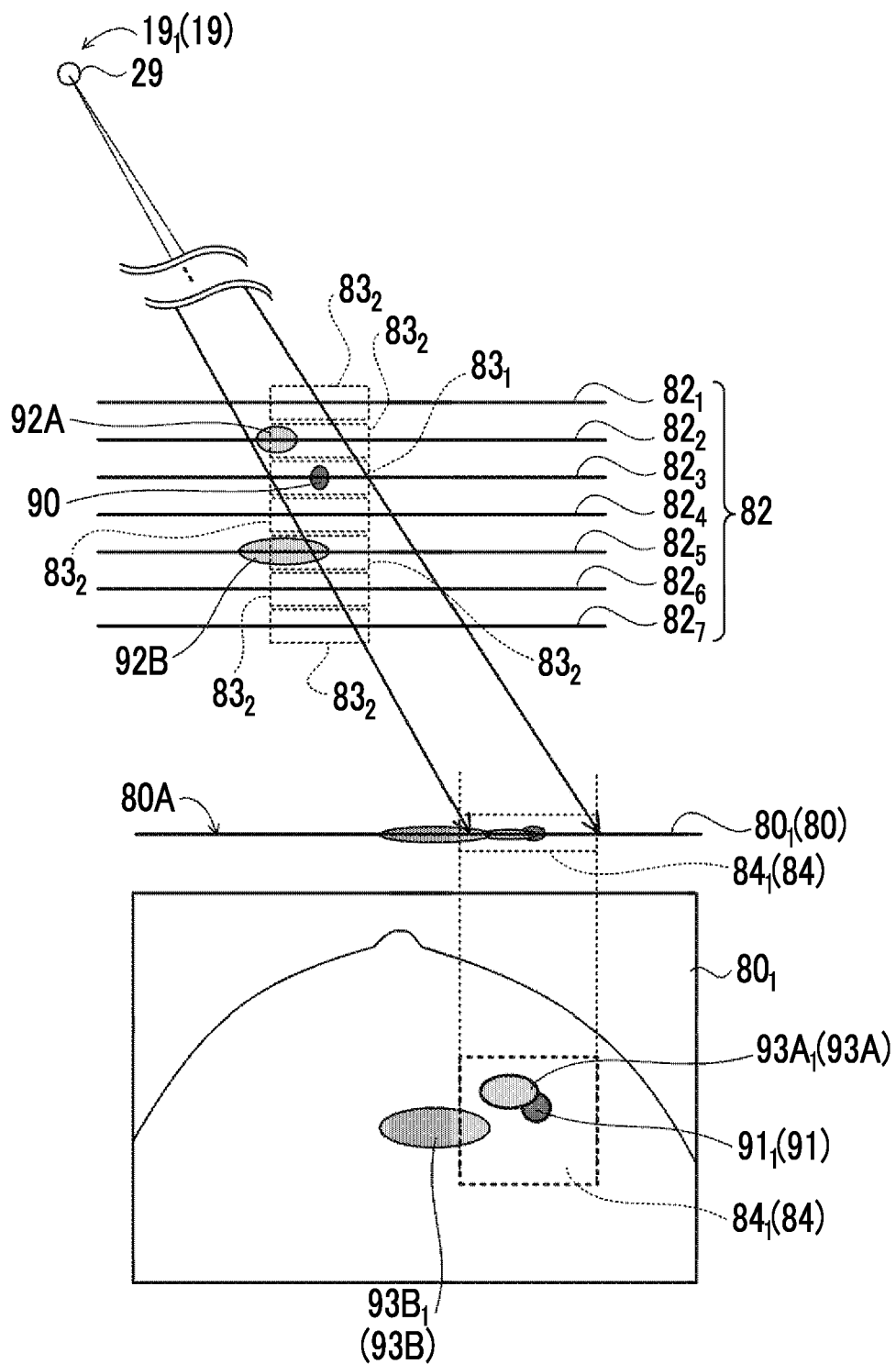
FIG. 5 is a diagram illustrating a correspondence relationship between projection images and tomographic images generated from a plurality of projection images.

An example of a method for generating the pseudo-projection image without a reference object in the pseudo-projection image generation unit 64 according to this embodiment will be described with reference to FIGS. 5 and 6. In addition, FIG. 5 illustrates a correspondence relationship between a projection image $80_1$ captured in a case in which the radiation source 29 is located at the irradiation position $19_1$ and tomographic images 82 generated from a plurality of projection images 80 including the projection image $80_1$. The projection image $80_1$ is used to generate the tomographic image 82. The projection image $80_1$ includes a structure image $93A_1$ indicating a structure 92A which is present at a height corresponding to a tomographic image $82_2$, a reference object image $91_1$ indicating a reference object 90 which is present at a height corresponding to a tomographic image $82_3$, and a structure image $93B_1$ indicating a structure 92B which is present at a height corresponding to a tomographic image $82_5$.

First, the pseudo-projection image generation unit 64 extracts the reference object 90 from the plurality of tomographic images 82 (seven tomographic images $82_1$ to $82_7$ in FIG. 5) with reference to FIG. 5. Specifically, the pseudo-projection image generation unit 64 extracts the reference object image 91 indicating the reference object 90 from the plurality of tomographic images 82. A method by which the pseudo-projection image generation unit 64 extracts the reference object image 91 will be described. In the case of the tomosynthesis imaging, as described above, imaging is performed at each irradiation position 19 to capture the plurality of projection images 80. Therefore, in some cases, the positional deviation between the projection images 80 occurs because of the influence of, for example, the movement of the object or the positional deviation of the radiation source 29 at each irradiation position 19. In the console 12 according to this embodiment, the positional deviation amount between the projection images 80 is derived using the reference object 90 as a reference. It is preferable that the reference object 90 has a characteristic structure, and an image indicating the reference object 90 is easily extracted from each of the tomographic image 82 and the projection image 80. In addition, it is preferable that the reference object 90 is included in all of the plurality of projection images 80 acquired by the image acquisition unit 60. Further, as described above, it is preferable that, since the reference object 90 is used as a reference for deriving the amount of positional deviation caused by, for example, the movement of the object, the reference object 90 is a structure which is present inside the object. Examples of the reference object 90 include at least one of a calcification or a mammary gland in a case in which the object is the breast. For example, in this embodiment, the mammary gland is predetermined as the reference object 90.

A method by which the pseudo-projection image generation unit 64 extracts the reference object 90 from the plurality of tomographic images 82 is not particularly limited. First, the pseudo-projection image generation unit 64 specifies, as a common region, a region that is included in all of the projection images 80 acquired by the image acquisition unit 60 in each of the plurality of tomographic images 82. A method by which the pseudo-projection image generation unit 64 specifies the common region is not particularly limited. For example, in this embodiment, imaging information indicating the irradiation angle range and the irradiation field is given to the plurality of projection images 80 obtained by the tomosynthesis imaging, and a correspondence relationship among the irradiation angle range, the irradiation field, and the common region in the tomosynthesis imaging is predetermined. The pseudo-projection image generation unit 64 specifies the common region from the correspondence relationship on the basis of the imaging information given to the plurality of projection images 80 acquired by the image acquisition unit 60.

In a case in which the common region is specified, the pseudo-projection image generation unit 64 extracts the mammary gland from the common region in each of the plurality of tomographic images 82. In addition, a method by which the pseudo-projection image generation unit 64 extracts the mammary gland is not particularly limited. The pseudo-projection image generation unit 64 according to this embodiment extracts a specific structure indicating the mammary gland from the common region in each of the tomographic images 82, using, for example, a known computer-aided diagnosis (hereinafter, referred to as CAD) algorithm. In the CAD algorithm, preferably, the probability (for example, likelihood) that a pixel in the common region will be the mammary gland is derived, and the pixel is detected as a pixel constituting the image of the mammary gland in a case in which the probability is equal to or greater than a predetermined threshold value. Further, for example, the pseudo-projection image generation unit 64 may use a method which extracts the mammary gland from the common region with a filtering process or the like using a filter for extracting the mammary gland. In a case in which a plurality of mammary glands are extracted, for example, in a case in which the mammary glands are extracted from each specific region in the plurality of tomographic images 82, the pseudo-projection image generation unit 64 extracts one mammary gland as the reference object 90 on the basis of feature amounts of the mammary glands. FIG. 5 illustrates an example in which the pseudo-projection image generation unit 64 extracts the reference object 90 from the tomographic image $82_3$. In this embodiment, the tomographic image $82_3$ is an example of a first tomographic image according to the present disclosure, and the tomographic images $82_1$, $82_2$, and $82_4$ to $82_7$ are examples of a second tomographic image according to the present disclosure.

Then, the pseudo-projection image generation unit 64 specifies a reference object region $83_1$ which is a portion including the reference object image 91 indicating the reference object 90 in the tomographic image $82_3$. In addition, a method by which the pseudo-projection image generation unit 64 specifies the reference object region $83_1$ is not particularly limited. In this embodiment, in the projection image $80_4$ captured at the irradiation position $19_4$ (see FIG. 2) where the irradiation angle α is 0 degrees, a region, which has the reference object image 91 of the reference object 90 as the center and which has a size that is a predetermined percentage of the size of the projection image $80_4$, is the reference object region $83_1$. Further, as illustrated in FIG. 5, the pseudo-projection image generation unit 64 specifies a region, which corresponds to the reference object region $83_1$, in each of the tomographic images $82_1$, $82_2$, and $82_4$ to $82_7$ as a partial region $83_2$.

Figure 6:
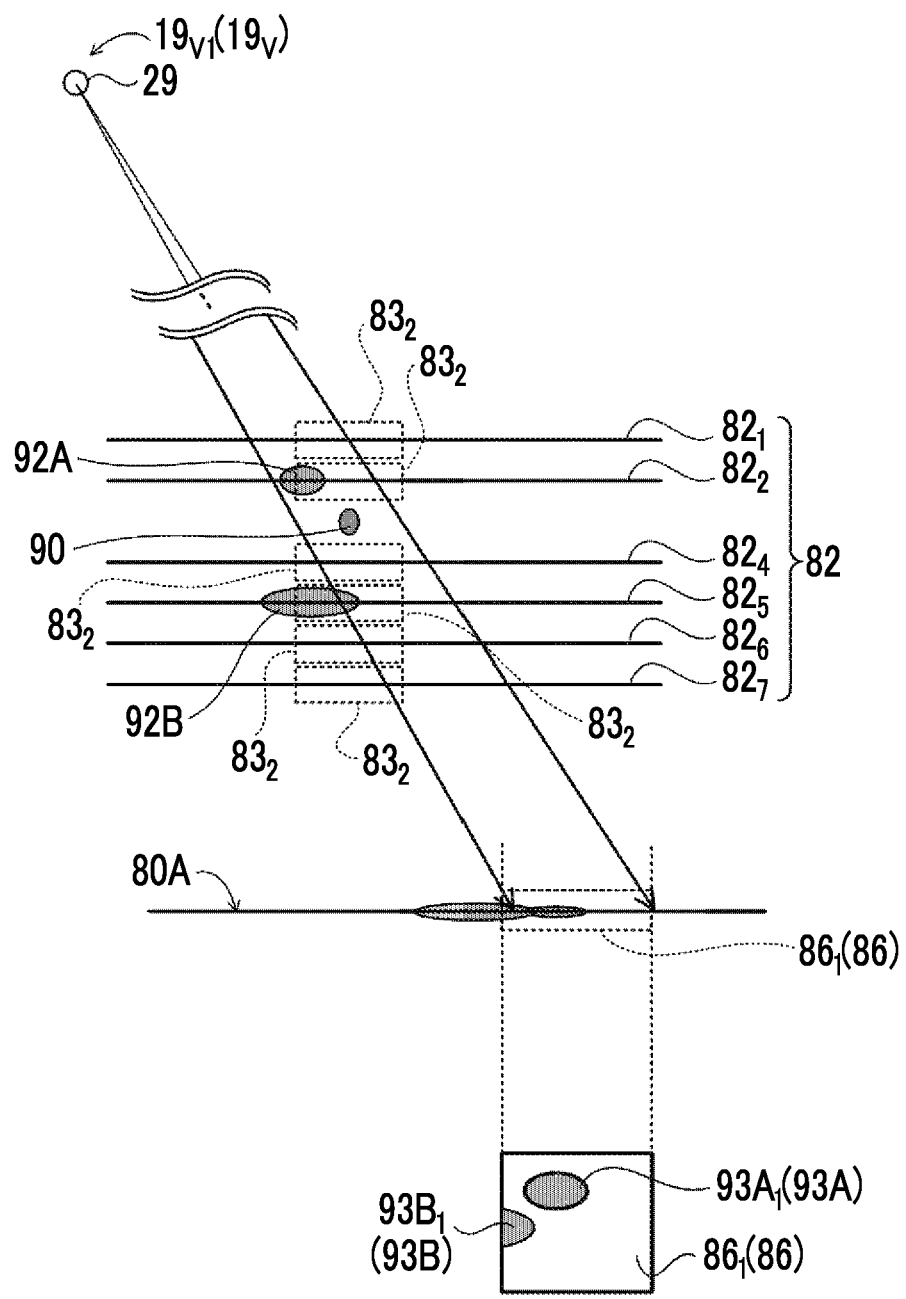
FIG. 6 is a diagram illustrating the generation of a pseudo-projection image without a reference object by a pseudo-projection image generation unit.

Then, as illustrated in FIG. 6, the pseudo-projection image generation unit 64 performs pseudo-projection at set irradiation positions $19_V$ (in FIG. 6, the irradiation position $19_{V1}$) corresponding to each of the irradiation positions 19 of the plurality of projection images 80, using the tomographic images $82_1$, $82_2$, and $82_4$ to $82_7$, to generate a plurality of pseudo-projection images without a reference object which do not include the reference object 90. The set irradiation position $19_V$ is the original irradiation position in the tomosynthesis imaging and is, for example, a design irradiation position. The irradiation position 19, which is the actual position of the radiation source 29 in a case in which the projection image 80 is captured in the tomosynthesis imaging, may deviate from the set irradiation position $19_V$ because of, for example, a change over time. In this embodiment, the set irradiation position $19_V$ is known, and the actual irradiation position 19 is unknown. Therefore, the pseudo-projection image generation unit 64 performs pseudo-projection on the partial region $83_2$ in each of the tomographic images $82_1$, $82_2$, and $82_4$ to $82_7$ at the set irradiation positions $19_V$ to generate pseudo-projection images 86 without a reference object in a same projection plane 80A as the projection images 80. In addition, in a case in which it is considered that the positional deviation of the irradiation position 19 of the radiation source 29 in the tomosynthesis imaging has not occurred, the set irradiation positions $19_V$ are the same as the actual irradiation positions 19. The pseudo-projection image 86 without a reference object according to this embodiment is an example of a pseudo-projection image without a reference object according to the present disclosure and is also an example of a partial pseudo-projection image.

The pseudo-projection image 86 without a reference object includes a structure image indicating a structure other than the reference object 90. In the example illustrated in FIG. 6, the pseudo-projection image $86_1$ without a reference object includes the structure image $93A_1$ indicating the structure 92A that is present at the height corresponding to the tomographic image $82_2$ and the structure image $93B_1$ indicating the structure 92B that is present at the height corresponding to the tomographic image $82_5$. Further, the pseudo-projection image $86_1$ without a reference object does not include the reference object image 91 indicating the reference object 90 that is present at the height corresponding to the tomographic image $82_3$. In this way, the pseudo-projection image generation unit 64 generates the pseudo-projection images 86 without a reference object at each of the set irradiation positions $19_V$.

The pseudo-projection image generation unit 64 outputs image data indicating the generated plurality of pseudo-projection images 86 without a reference object to the positional deviation amount derivation unit 66.

The positional deviation amount derivation unit 66 has a function of deriving the positional deviation amount between the projection images 80. As illustrated in FIG. 4, the positional deviation amount derivation unit 66 according to this embodiment includes a component-removed image generation unit 67. The component-removed image generation unit 67 has a function of generating component-removed images which include the reference object and which are obtained by removing components of the plurality of pseudo-projection images 86 without a reference object from the plurality of projection images 80.

First, as illustrated in FIG. 5, the component-removed image generation unit 67 according to this embodiment extracts an image of a portion corresponding to the pseudo-projection image 86 without a reference object as a partial image 84 from the projection image 80. Further, as illustrated in FIG. 7, the component-removed image generation unit 67 subtracts pixel values of the pseudo-projection images 86 without a reference object from pixel values of the extracted partial images 84 for each corresponding pixel to generate component-removed images 88 (component-removed images $88_1$ to $88_7$ in FIG. 7) indicating the difference between the partial images 84 and the pseudo-projection images 86 without a reference object.

Figure 7:
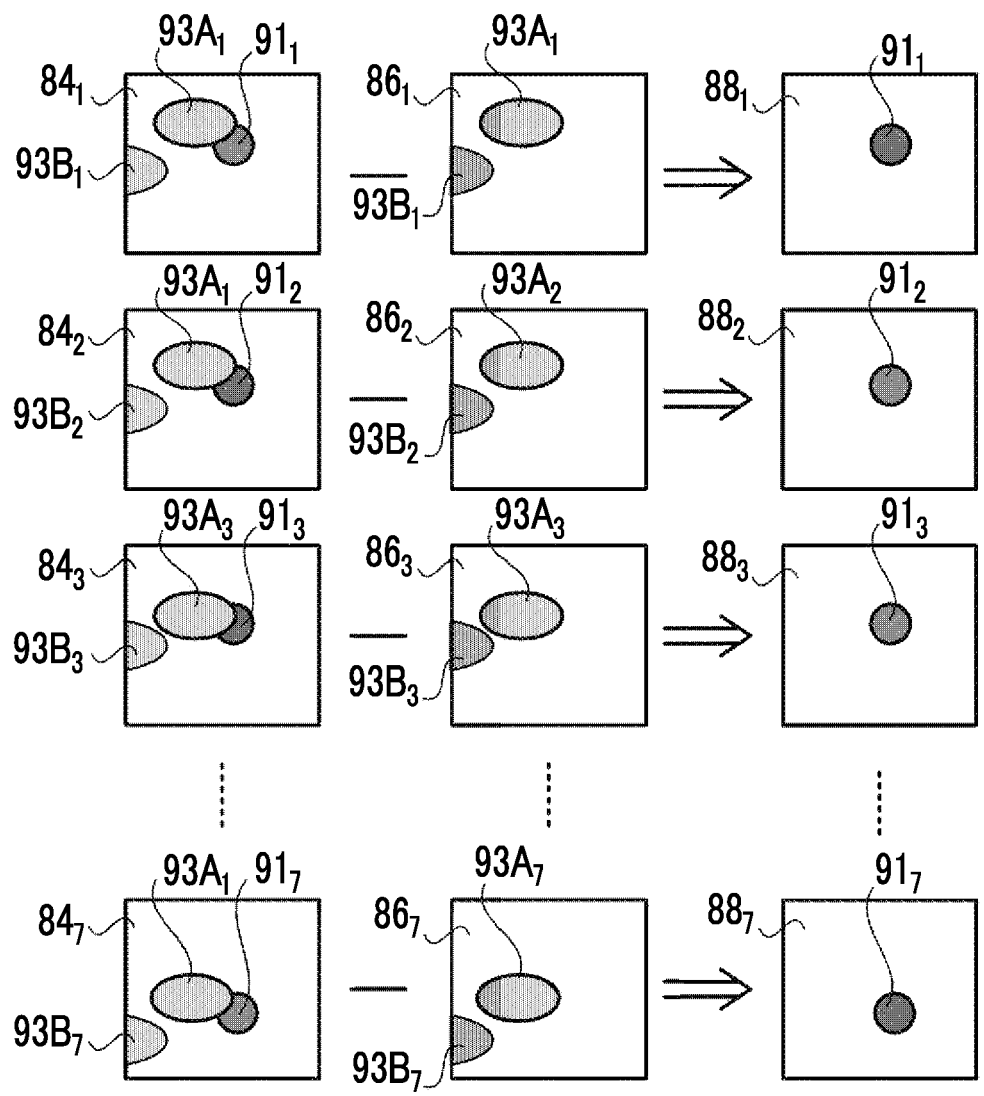
FIG. 7 is a diagram illustrating the generation of a component-removed image by a component-removed image generation unit.

Specifically, as illustrated in FIG. 7, the component-removed image generation unit 67 subtracts the pixel value of the pseudo-projection image $86_1$ without a reference object from the pixel value of the partial image $84_1$ for each corresponding pixel in the projection image $80_1$ corresponding to the irradiation position $19_1$, which is the initial irradiation position 19, to generate the component-removed image $88_1$. In addition, the component-removed image generation unit 67 subtracts the pixel value of the pseudo-projection image $86_2$ without a reference object from the pixel value of the partial image $84_2$ for each corresponding pixel in the projection image $80_2$ corresponding to the irradiation position $19_2$ to generate the component-removed image $88_2$. Further, the component-removed image generation unit 67 subtracts the pixel value of the pseudo-projection image $86_3$ without a reference object from the pixel value of the partial image $84_3$ for each corresponding pixel in the projection image $80_3$ corresponding to the irradiation position $19_3$ to generate the component-removed image $88_3$. In this way, the component-removed image generation unit 67 generates the component-removed images 88 from the partial images 84 of the projection images 80 corresponding to each irradiation position 19 and the pseudo-projection images 86 without a reference object and subtracts the pixel value of the pseudo-projection image $86_7$ without a reference object from the pixel value of the partial image $84_7$ for each corresponding pixel in the projection image $80_7$ corresponding to the irradiation position $19_7$, which is the last irradiation position 19, to generate the component-removed image $88_7$.

The projection image 80 has structures arranged in a direction in which the radiation R is emitted and includes a large amount of information. Therefore, as illustrated in FIGS. 5 to 7, the reference object image 91 and the structure images 93A and 93B are included in the projection image 80 according to this embodiment in a state in which they are superimposed according to the height at which the reference object 90 and the structures 92A and 92B are present. In the example illustrated in FIGS. 5 and 6, the structure 92A is present on the reference object 90. Therefore, the structure images $93A_1$ to $93A_7$ are included in the partial images $84_1$ to $84_7$ illustrated in FIG. 7 in a state in which they are superimposed on the reference object images $91_1$ to $91_7$, respectively. As described above, in a case in which an image of another structure, such as the structure image 93A, is superimposed on the reference object image 91, the image of another structure, such as the structure image 93A, makes it difficult to extract the contour of the reference object image 91.

In contrast, in the component-removed images $88_1$ to $88_7$, the structure images 93A and 93B which are the images of other structures have been removed. Therefore, the reference object image 91 does not overlap with other structure images and is clearly shown. In particular, in the component-removed images $88_1$ to $88_7$, the structure image 93A indicating the structure 92A which is present above the reference object 90, that is, on a side closer to the radiation source 29 than the reference object 90, and which is superimposed on the reference object image 91, has been removed. Therefore, the reference object image 91 is clearly shown.

In addition, the aspect in which the component-removed image generation unit 67 according to this embodiment subtracts the pixel value of the pseudo-projection image 86 without a reference object from the pixel value of the partial image 84 for each corresponding pixel to generate the component-removed image 88 has been described. However, the method by which the component-removed image generation unit 67 generates the component-removed image 88 is not limited to this aspect. For example, the component-removed image generation unit 67 may reduce the pixel values of pixels, which are correlated with the pseudo-projection image 86 without a reference object, in each partial image 84 to generate the component-removed image 88.

The positional deviation amount derivation unit 66 derives the positional deviation amount between the projection images 80 on the basis of the component-removed images $88_1$ to $88_7$ generated by the component-removed image generation unit 67. A method by which the positional deviation amount derivation unit 66 derives the positional deviation amount between the projection images 80 is not limited. For example, the positional deviation amount derivation unit 66 according to this embodiment derives the positional deviation amount between the projection images 80 on the basis of the component-removed images $88_1$ to $88_7$ and the tomographic image $82_3$. As an example of a specific method, the positional deviation amount derivation unit 66 according to this embodiment applies the technique described in WO2020/067475A to derive the positional deviation amount between the projection images 80. WO2020/067475A discloses a technique which derives the positional deviation amount between a plurality of projection images on the basis of a feature point in a tomographic plane corresponding to a tomographic image in which the feature point has been detected. In a case in which this technique is applied to this embodiment, the positional deviation amount derivation unit 66 uses each projection image 80 as a tomographic plane projection image projected onto the tomographic plane of the tomographic image $82_3$ and derives the positional deviation amount between the projection images 80 on the basis of the positional deviation amount between a plurality of tomographic plane projection images derived on the basis of the feature point of the reference object 90. The positional deviation amount derivation unit 66 may derive, for example, the positional deviation amount for each partial image 84 as the positional deviation amount between the projection images 80. Further, the positional deviation amount derivation unit 66 may derive, for example, the positional deviation amount of the entire breast which is the object between the projection images 80 as the positional deviation amount between the projection images 80. In a case in which the positional deviation amount of the entire breast between the projection images 80 is derived, for example, a method may be applied which sets a parameter indicating the positional deviation amount of the entire breast and which optimizes the parameter according to the positional deviation of the reference object 90.

The positional deviation amount between the projection images 80 derived by the positional deviation amount derivation unit 66 is output to the notification unit 68 and the tomographic image generation unit 70.

In a case in which the positional deviation amount between the projection images 80 is relatively large, it may be difficult to sufficiently correct the positional deviation between the projection images 80, or the quality of the tomographic images 82 generated from the projection images 80 may deteriorate. For example, in a case in which the subject makes a large movement during the tomosynthesis imaging, the movement of the breast, which is the object, may be large, or the positional deviation amount between the projection images 80 may be relatively large. In this case, for example, it is preferable to capture the projection images 80 again. Therefore, the notification unit 68 according to this embodiment has a function of notifying of a warning in a case in which the positional deviation amount derived by the positional deviation amount derivation unit 66 is greater than a predetermined threshold value. The predetermined threshold value used to determine whether or not to notify of the warning may be predetermined according to, for example, the desired quality of the tomographic image 82 or the accuracy of diagnosis, or may be set by the user. For example, in this embodiment, the positional deviation amount where it is preferable to perform re-imaging is set as the predetermined threshold value. In addition, a notification method by the notification unit 68 is not particularly limited. For example, the warning may be displayed on the display unit 58 of the console 12 by at least one of visible display or audible display. Further, the content of which notification is sent by the notification unit 68 is not limited to the warning. At least one of a visual notification method or an auditory notification method may be used. For example, a warning message may be displayed on the display unit 58 of the console 12, or a warning sound may be output by a speaker (not shown) of the console 12. Furthermore, the content of which notification is sent by the notification unit 68 is not limited to the warning, and the specific content of the notification is not limited. For example, the content may be information indicating that the positional deviation amount is large or the positional deviation amount.

The tomographic image generation unit 70 has a function of generating a plurality of tomographic images in each of a plurality of tomographic planes on the basis of the plurality of projection images 80 acquired by the image acquisition unit 60 and the positional deviation amount derived by the positional deviation amount derivation unit 66. A method by which the tomographic image generation unit 70 generates the plurality of tomographic images in each of the plurality of tomographic planes on the basis of the plurality of projection images 80 and the positional deviation amount is not limited. For example, in a case in which the tomographic image generation unit 70 reconstructs the tomographic images from the plurality of projection images 80 using a back projection method, it reconstructs the tomographic images, using back projection positions of the projection images 80 corrected on the basis of the positional deviation amount, to generate a plurality of tomographic images. Further, for example, the tomographic image generation unit 70 corrects the projection images 80 on the basis of the positional deviation amount to obtain a plurality of projection images assuming that no positional deviation has occurred. Then, the tomographic image generation unit 70 may generate a plurality of tomographic images using the plurality of projection images 80 whose positional deviation has been corrected.

In addition, the height of a plurality of tomographic planes generated by the tomographic image generation unit 70 is not limited. For example, the height of the tomographic planes may be the same as or different from the height of the plurality of tomographic images 82 acquired by the tomographic image acquisition unit 62. Further, the height of the tomographic planes may be designated by the user.

The tomographic image generation unit 70 outputs image data indicating the generated plurality of tomographic images to the display control unit 72.

The display control unit 72 has a function of displaying the plurality of tomographic images generated by the tomographic image generation unit 70 on the display unit 58. In addition, the display destination of the plurality of tomographic images is not limited to the display unit 58. For example, the display destination may be an image reading device or the like outside the radiography system 1.

Next, the operation of the console 12 in the tomosynthesis imaging will be described with reference to the drawings. After the mammography apparatus 10 performs the tomosynthesis imaging, the console 12 generates a plurality of tomographic images using a plurality of projection images obtained by the tomosynthesis imaging and displays the tomographic images on, for example, the display unit 58.

For example, in a case in which the tomosynthesis imaging ends, the mammography apparatus 10 according to this embodiment outputs image data of a plurality of captured projection images 80 to the console 12. The console 12 stores the image data of the plurality of projection images 80 input from the mammography apparatus 10 in the storage unit 52.

Figure 8:
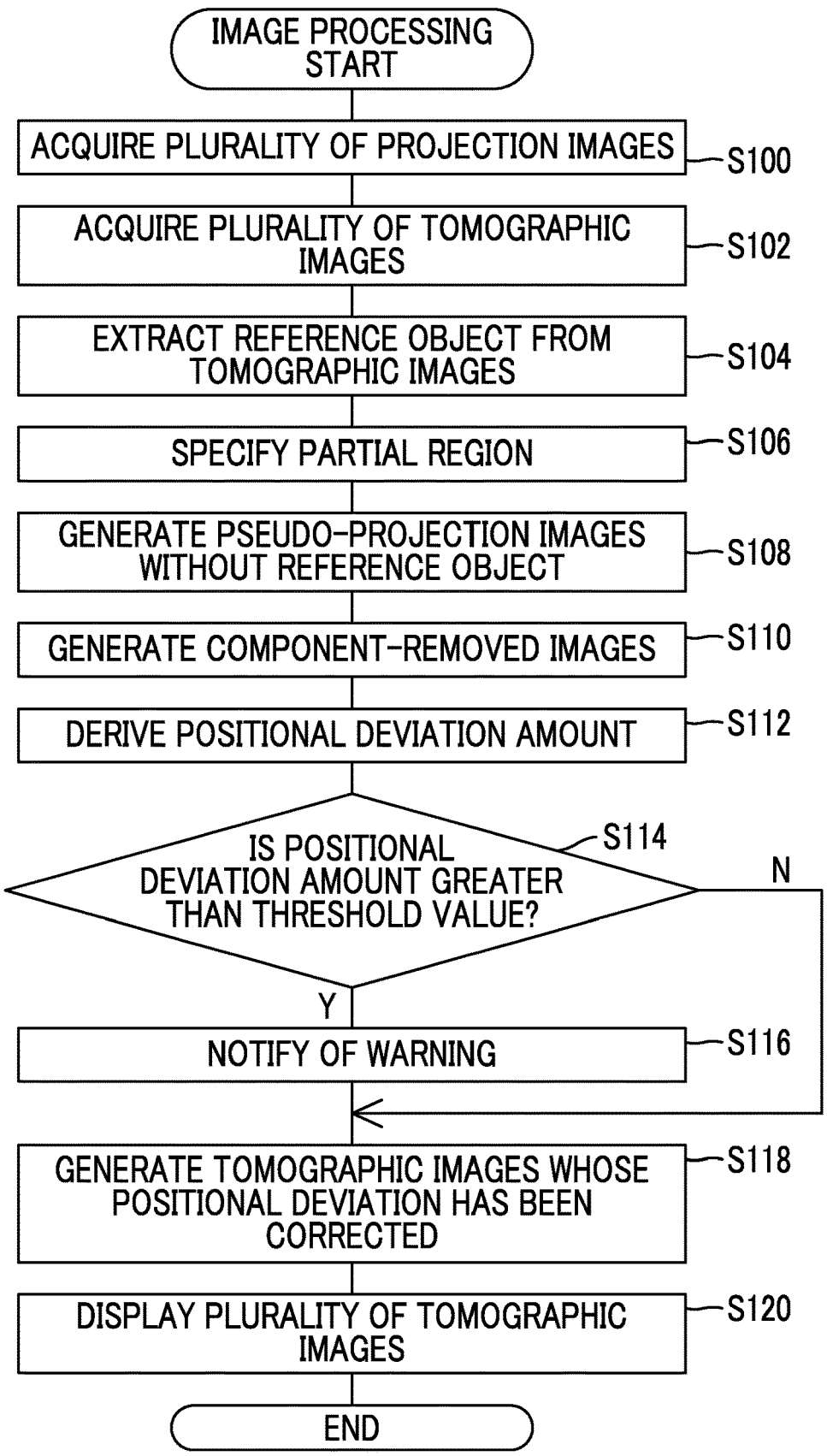
FIG. 8 is a flowchart illustrating an example of the flow of image processing by the console according to the first embodiment.

After storing the image data of the plurality of projection images 80 in the storage unit 52, the console 12 performs image processing illustrated in FIG. 8. FIG. 8 is a flowchart illustrating an example of the flow of the image processing performed by the console 12 according to this embodiment. In the console 12 according to this embodiment, for example, the CPU 50A of the control unit 50 executes the image generation program 51 stored in the ROM 50B to perform the image processing whose example is illustrated in FIG. 8.

In Step S100 of FIG. 8, the image acquisition unit 60 acquires a plurality of projection images 80. As described above, the image acquisition unit 60 according to this embodiment acquires image data of the plurality of projection images from the storage unit 52.

Then, in Step S102, the tomographic image acquisition unit 62 acquires a plurality of tomographic images 82. As described above, a plurality of tomographic images 82 corresponding to each of a plurality of tomographic planes of the breast are generated using the plurality of projection images 80 acquired in Step S100. Then, the plurality of tomographic images 82 are acquired.

Then, in Step S104, the pseudo-projection image generation unit 64 extracts the reference object 90 used as a reference for deriving the positional deviation amount between the projection images 80 from the plurality of tomographic images 82. As described above, the pseudo-projection image generation unit 64 extracts the reference object 90 which is the mammary gland from the common region of the plurality of projection images 80 on the basis of the feature amount.

Then, in Step S106, the pseudo-projection image generation unit 64 specifies the partial region 83 in the tomographic image 82 that does not include the reference object image 91 indicating the reference object 90. As described above, the pseudo-projection image generation unit 64 specifies the reference object region $83_1$ including the reference object image 91 indicating the reference object 90 extracted in Step S104 and specifies the partial region $83_2$, which corresponds to the specified reference object region $83_1$, in other tomographic images 82. In this embodiment, as described above, the pseudo-projection image generation unit 64 specifies the reference object region $83_1$ in the tomographic image $82_3$. In addition, the pseudo-projection image generation unit 64 specifies, as the partial region $83_2$, a region corresponding to the reference object region $83_1$ in each of the tomographic images $82_1$, $82_2$, and $82_4$ to $82_7$.

Then, in Step S108, the pseudo-projection image generation unit 64 generates the pseudo-projection images 86 without a reference object. As described above, the pseudo-projection image generation unit 64 performs pseudo-projection on the partial region $83_2$ in each of the tomographic images $82_1$, $82_2$, and $82_4$ to $82_7$ at the set irradiation positions $19_r$ to generate the pseudo-projection images 86 without a reference object in the projection plane 80A of the projection images 80.

Then, in Step S110, the component-removed image generation unit 67 of the positional deviation amount derivation unit 66 generates the component-removed images 88. As described above, the component-removed image generation unit 67 extracts the image of a portion, which corresponds to the pseudo-projection image 86 without a reference object, as the partial image 84 from the plurality of projection images 80. Further, the component-removed image generation unit 67 subtracts the pixel value of the pseudo-projection image 86 without a reference object from the pixel value of the extracted partial image 84 for each corresponding pixel to generate the component-removed image 88 indicating the difference between the partial image 84 and the pseudo-projection image 86 without a reference object.

Then, in Step S112, the positional deviation amount derivation unit 66 derives the positional deviation amount between the plurality of projection images 80. As described above, the positional deviation amount derivation unit 66 derives the positional deviation amount between the projection images 80 on the basis of the component-removed images 88 generated in Step S110.

Then, in Step S114, the notification unit 68 determines whether or not the positional deviation amount between the plurality of projection images 80 is greater than a predetermined threshold value. In other words, as described above, the notification unit 68 determines whether or not the positional deviation amount is equal to or greater than a value at which it is preferable to perform re-imaging. In a case in which the positional deviation amount derived in Step S112 is equal to or less than the predetermined threshold value, the determination result in Step S114 is "No", and the process proceeds to Step S118. On the other hand, in a case in which the positional deviation amount derived in Step S112 is greater than the predetermined threshold value, the determination result in Step S114 is "Yes", and the process proceeds to Step S116.

In Step S116, the notification unit 68 displays a warning on the display unit 58. As described above, the notification unit 68 according to this embodiment notifies the user of a warning indicating that it is preferable to perform re-imaging since the positional deviation amount is large, using the display unit 58.

Then, in Step S118, the tomographic image generation unit 70 generates a plurality of tomographic images whose positional deviation has been corrected. As described above, the tomographic image generation unit 70 generates a plurality of tomographic images in each of a plurality of tomographic planes on the basis of the plurality of projection images 80 acquired in Step S100 and the positional deviation amount derived in Step S112.

Then, in Step S120, the display control unit 72 displays the tomographic images generated in Step S118 on the display unit 58. In a case in which the process in Step S120 ends, the image processing illustrated in FIG. 8 ends.

As described above, the console 12 according to this embodiment processes a plurality of projection images 80 obtained by irradiating the breast with the radiation R emitted from the radiation source 29 at each of the plurality of irradiation positions 19 having different irradiation angles α. The console 12 comprises the CPU 50A. The CPU 50A acquires a plurality of projection images 80, acquires a plurality of tomographic images 82 which are generated using the plurality of projection images 80 and correspond to each of a plurality of tomographic planes of the breast, performs pseudo-projection at the set irradiation positions $19_V$ corresponding to each of the irradiation positions 19 of the plurality of projection images 80, using a group of the tomographic images 82 ($82_1$, $82_2$, and $82_4$ to $82_7$) other than the tomographic image $82_1$ including the reference object image 91 indicating the reference object 90 used as a reference for deriving the positional deviation amount between the projection images 80 among the plurality of tomographic images 82, to generate a plurality of pseudo-projection images 86 without a reference object that do not include the reference object image 91 indicating the reference object 90, and derives the positional deviation amount between the projection images 80 on the basis of the component-removed images 88 which include the reference object image 91 and are obtained by removing the components of the plurality of pseudo-projection images 86 without a reference object from the plurality of projection images 80.

The console 12 according to this embodiment derives the positional deviation amount between the projection images 80 using the reference object 90 which is a reference for deriving the positional deviation amount between the projection images 80. The projection image 80 has structures arranged in a direction in which the radiation R is emitted and includes a large amount of information. Therefore, the projection image 80 includes a structure image indicating a structure other than the reference object 90 in addition to the reference object image 91 indicating the reference object 90. The projection image 80 illustrated in FIG. 5 includes the structure image 93A indicating the structure 92A and the structure image 93B indicating the structure 92B in addition to the reference object image 91. In a case in which the image of another structure is superimposed on the reference object image 91, the contour of the reference object image 91 is unclear. In particular, a structure image indicating a structure that is present above the reference object 90, in other words, on the side close to the radiation source 29 (the structure image 93A indicating the structure 92A in this embodiment) is superimposed on the reference object image 91. Therefore, in particular, the contour of the reference object image 91 is unclear.

Therefore, the console 12 according to this embodiment derives the positional deviation amount between the projection images 80 on the basis of the component-removed images 88 generated by subtracting the pixel values of a plurality of pseudo-projection images 86 without a reference object that do not include the reference object image 91 from the pixel values of the partial images 84 of the projection images 80 for each corresponding pixel. As described above, the console 12 according to this embodiment derives the positional deviation amount between the projection images 80 using the component-removed images 88 in which the reference object image 91 indicating the reference object 90 is clearly shown. Therefore, the console 12 according to this embodiment can derive the positional deviation amount between the projection images 80 with high accuracy.

In addition, the correction of the positional deviation in Step S118 may not be sufficient. In other words, in some cases, the quality of the plurality of tomographic images generated by the tomographic image generation unit 70 in Step S118 is lower than the quality of a plurality of tomographic images generated from the projection images 80 in a case in which it is considered that no positional deviation has occurred. In this case, until the positional deviation amount derived in Step S112 is equal to or less than a value at which it is considered that no positional deviation has occurred, the process may return to Step S106 after Step S118, and the processes in Steps S106 to S116 may be repeated.

Further, in this embodiment, the aspect in which the pseudo-projection image generation unit 64 performs pseudo-projection on the partial region $83_2$, which corresponds to the reference object region $83_1$, in the tomographic images 82 to generate the pseudo-projection images 86 without a reference object has been described. However, the region on which the pseudo projection is performed is not limited to this aspect. For example, the pseudo-projection image generation unit 64 may perform pseudo-projection on the entire tomographic image 82 to generate the pseudo-projection image 86 without a reference object.

Second Embodiment

Since the overall configuration of a radiography system 1 according to this embodiment is the same as that of the radiography system 1 (see FIG. 1) according to the first embodiment, the detailed description thereof will not be repeated. Further, since the configuration of a mammography apparatus 10 is the same as that of the mammography apparatus 10 (see FIGS. 1 to 3) according to the first embodiment, the detailed description thereof will not be repeated.

Figure 9:
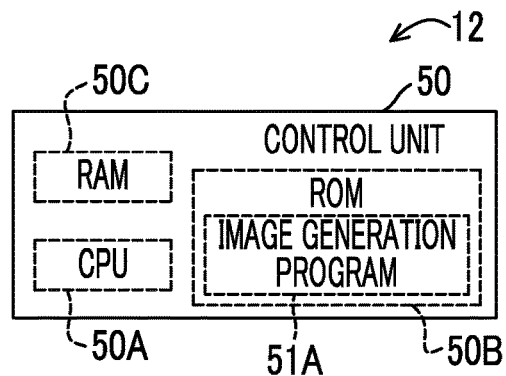
FIG. 9 is a block diagram illustrating an example of the configuration of a control unit of a console according to a second embodiment.

Further, since the hardware configuration of the console 12 according to this embodiment is the same as that in the first embodiment except that an image generation program 51A is stored in the ROM 50B of the control unit 50 instead of the image generation program 51 according to the first embodiment as illustrated in FIG. 9, the description thereof will not be repeated.

Figure 10:
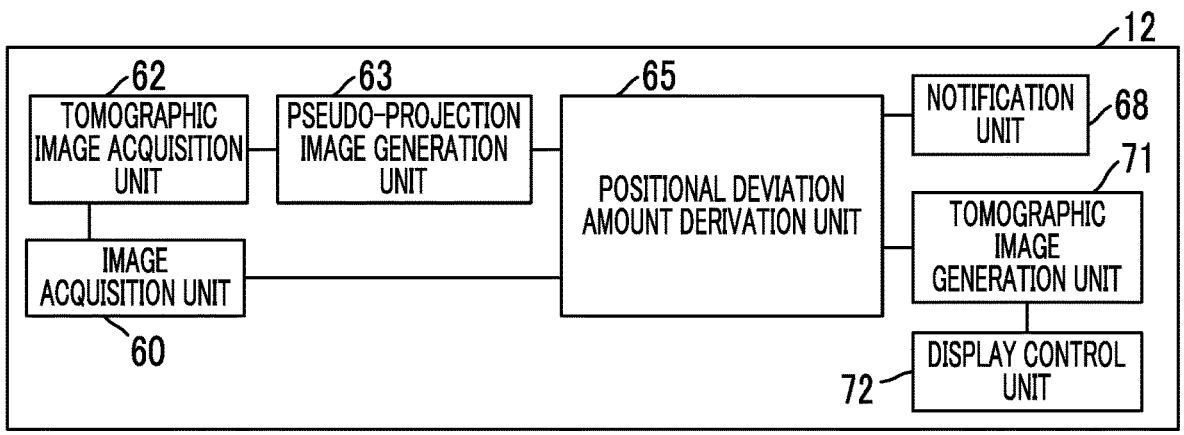
FIG. 10 is a functional block diagram illustrating an example of the functions of the console according to the second embodiment.

On the other hand, since the functional configuration of the console 12 according to this embodiment is different from that of the console 12 (see FIG. 4) according to the first embodiment, the functional configuration of the console 12 according to this embodiment will be described. FIG. 10 is a functional block diagram illustrating an example of a configuration related to a function of correcting the positional deviation between a plurality of projection images 80 obtained by the tomosynthesis imaging in the console 12 according to this embodiment. As illustrated in FIG. 10, the console 12 comprises an image acquisition unit 60, a tomographic image acquisition unit 62, a pseudo-projection image generation unit 63, a positional deviation amount derivation unit 65, a notification unit 68, a tomographic image generation unit 71, and a display control unit 72. For example, in the console 12 according to this embodiment, the CPU 50A of the control unit 50 executes the image generation program 51A stored in the ROM 50B to function as the image acquisition unit 60, the tomographic image acquisition unit 62, the pseudo-projection image generation unit 63, the positional deviation amount derivation unit 65, the notification unit 68, the tomographic image generation unit 71, and the display control unit 72.

The image acquisition unit 60 has a function of acquiring a plurality of projection images 80, similarly to the image acquisition unit 60 (see FIG. 4) according to the first embodiment. Specifically, the image acquisition unit 60 according to this embodiment acquires image data indicating a plurality of projection images 80 obtained by the tomosynthesis imaging in the mammography apparatus 10. The image acquisition unit 60 outputs the acquired image data indicating the plurality of projection images 80 to the tomographic image acquisition unit 62 and to the positional deviation amount derivation unit 65.

Figure 11:
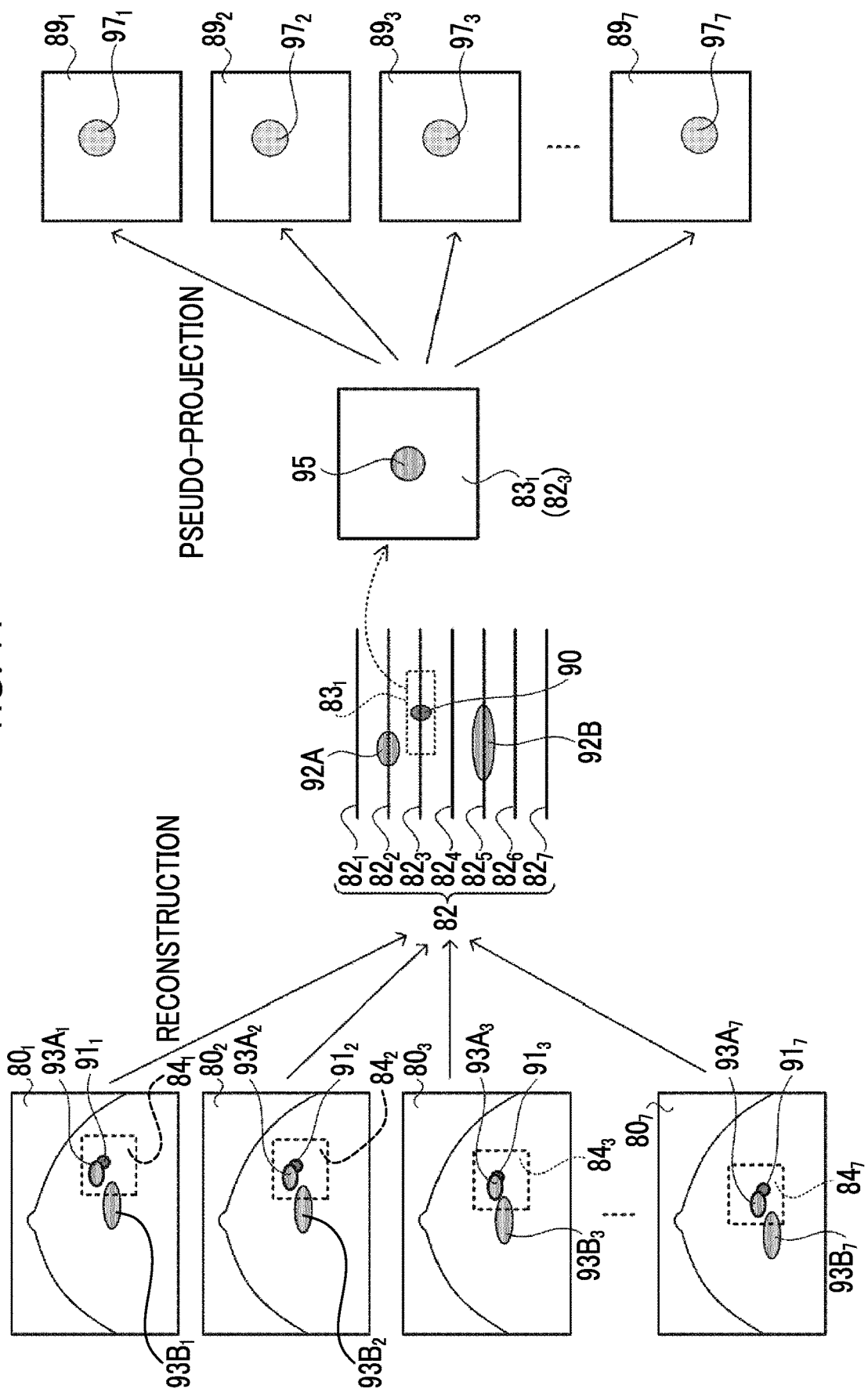
FIG. 11 is a diagram illustrating the generation of a pseudo-projection image with a reference object in the second embodiment.

Similarly to the tomographic image acquisition unit 62 (see FIG. 4) according to the first embodiment, the tomographic image acquisition unit 62 has a function of acquiring a plurality of tomographic images 82 corresponding to each of a plurality of tomographic planes of the breast as an object. Specifically, as illustrated in FIG. 11, the tomographic image acquisition unit 62 according to this embodiment reconstructs a plurality of projection images $80_1$ to $80_7$ acquired by the image acquisition unit 60 to generate a plurality of tomographic images $82_1$ to $82_7$ corresponding to each of the plurality of tomographic planes of the breast and acquires a plurality of tomographic images 82. The tomographic image acquisition unit 62 outputs image data indicating the generated plurality of tomographic images 82 to the pseudo-projection image generation unit 63.

The pseudo-projection image generation unit 63 has a function of performing pseudo-projection at the set irradiation positions $19_V$ corresponding to each of the irradiation positions 19 of the plurality of projection images 80, using a tomographic image 82 including a reference object image 95 indicating a reference object 90 used as a reference for deriving the positional deviation amount between the projection images 80 among the plurality of tomographic images 82 acquired by the tomographic image acquisition unit 62, to generate a plurality of pseudo-projection images including a reference object image 97. In this embodiment, the pseudo-projection image including the reference object image 97 is referred to as a "pseudo-projection image with a reference object".

An example of a method for generating the pseudo-projection image with a reference object in the pseudo-projection image generation unit 63 according to this embodiment will be described with reference to FIG. 5 illustrating the first embodiment and FIGS. 11 and 12.

First, the pseudo-projection image generation unit 63 extracts the reference object 90 from the plurality of tomographic images 82. Specifically, the pseudo-projection image generation unit 63 extracts the reference object image 95 indicating the reference object 90 from the plurality of tomographic images 82. In this embodiment, the reference object 90 used as a reference for deriving the positional deviation amount between the projection images 80 is the same as the reference object 90 in the first embodiment. Further, since a method by which the pseudo-projection image generation unit 63 extracts the reference object 90 from the plurality of tomographic images 82 is the same as the method by which the pseudo-projection image generation unit 64 according to the first embodiment extracts the reference object 90 from the plurality of tomographic images 82, the description thereof will not be repeated. Further, in this embodiment, similarly to the reference object 90 according to the first embodiment, a case in which the pseudo-projection image generation unit 63 extracts the reference object 90 that is present at the height corresponding to the tomographic image $82_3$ among the tomographic images $82_1$ to $82_7$ will be described.

Then, as illustrated in FIG. 11, the pseudo-projection image generation unit 63 specifies a reference object region $83_1$ which is a portion including the reference object image 95 indicating the reference object 90 in the tomographic image $82_3$. In addition, since a method by which the pseudo-projection image generation unit 63 specifies the reference object region $83_1$ is the same as the method by which the pseudo-projection image generation unit 64 according to the first embodiment specifies the reference object region $83_1$, the description thereof will not be repeated.

Figure 12:
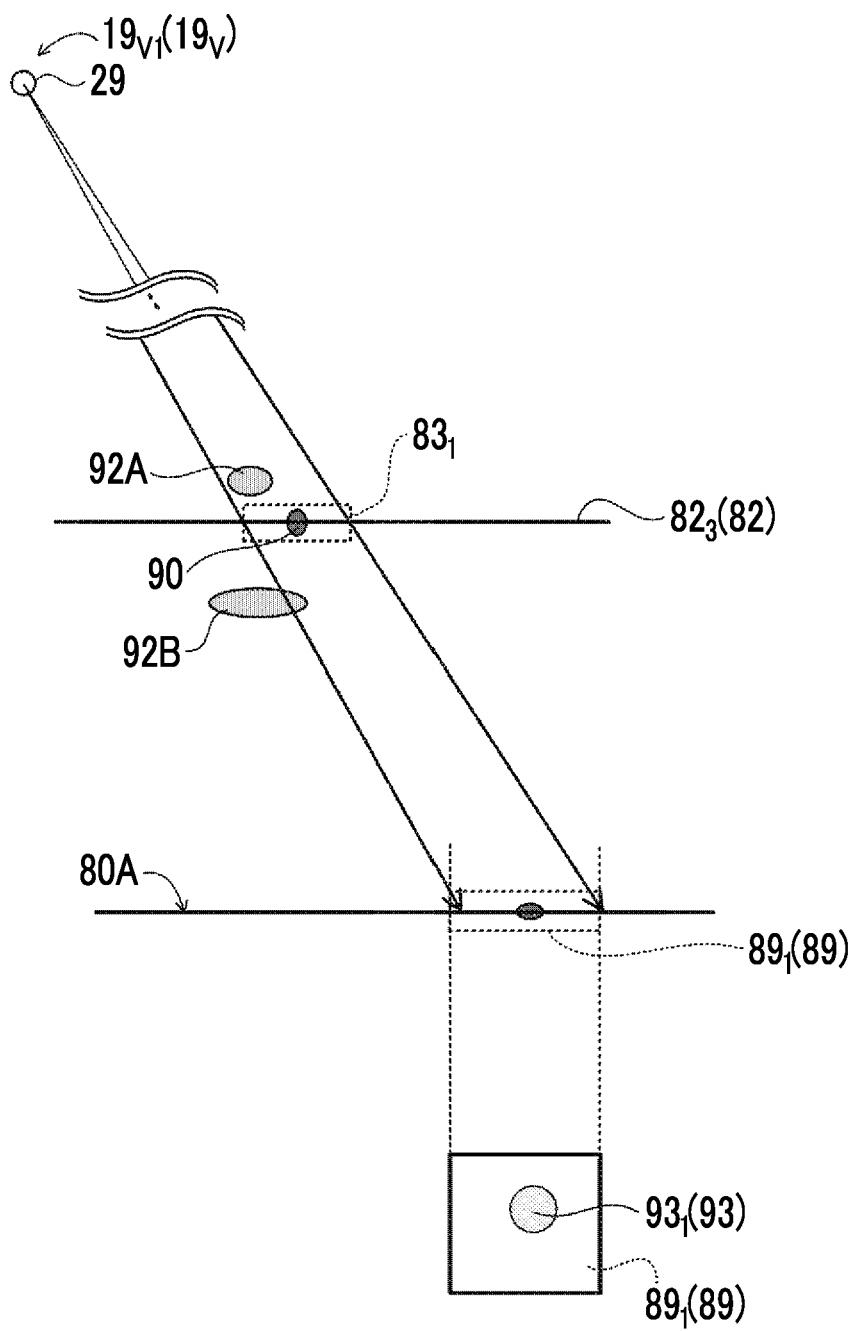
FIG. 12 is a diagram illustrating the generation of the pseudo-projection image with a reference object by a pseudo-projection image generation unit.

Then, as illustrated in FIGS. 11 and 12, the pseudo-projection image generation unit 63 performs pseudo-projection at the set irradiation positions $19_{V1}$ to $19_{V7}$ corresponding to each of the irradiation positions $19_1$ to $19_7$ of the projection images $80_1$ to $80_7$, using the reference object region $83_1$, to generate pseudo-projection images $89_1$ to $89_7$ with a reference object which include the reference object image 97. In addition, FIG. 12 illustrates the pseudo-projection image $89_1$ with a reference object which has been pseudo-projected onto the same projection plane 80A as the projection image 80 at the set irradiation position $19_{V1}$ corresponding to the irradiation position $19_1$.

An image indicating a structure included in the pseudo-projection image 89 with a reference object is determined according to an image indicating a structure included in the tomographic image $82_3$. In the example illustrated in FIGS. 11 and 12, the tomographic image $82_3$ includes the reference object image 95 indicating the reference object 90, but does not include a structure image indicating a structure 92A and a structure image indicating a structure 92B. Therefore, the pseudo-projection image 89 with a reference object includes the reference object image 95, but does not include the structure images indicating the structures 92A and 92B. Therefore, the pseudo-projection image 89 with a reference object is an image that does not include a structure image indicating a structure which is present at a position different from that of the reference object 90.

For example, in some cases, blurring occurs in the tomographic images 82 generated from the plurality of projection images 80 having a positional deviation therebetween due to the influence of the positional deviation. For example, in the example illustrated in FIG. 11, the reference object image 95 included in the tomographic image 82$_3$ is more blurred or has a larger size than the reference object image 91 included in the projection image 80. Further, since the reference object region 83$_1$ including the reference object image 95 affected by the positional deviation is pseudo-projected, the reference object image 97 included in the pseudo-projection image 89 with a reference object is more blurred or has a larger size than the reference object image 91 included in the projection image 80. As described above, the pseudo-projection image 89 with a reference object includes the reference object image 97 in which the positional deviation between the projection images 80 appears.

The pseudo-projection image generation unit 63 outputs image data indicating the generated plurality of pseudo-projection images 89 with a reference object to the positional deviation amount derivation unit 65.

The positional deviation amount derivation unit 65 has a function of deriving the positional deviation amount between the projection images 80 on the basis of the projection images 80$_1$ to 80$_7$ and the pseudo-projection images 89$_1$ to 89$_7$ with a reference object. As described above, the pseudo-projection image 89 with a reference object includes the reference object image 97 in which the positional deviation between the projection images 80 appears. For example, the reference object image 97 of the pseudo-projection image 89 with a reference object is larger than the reference object image 91 of the projection image 80. The positional deviation amount derivation unit 65 according to this embodiment compares the reference object image 97 included in the pseudo-projection image 89 with a reference object with the reference object image 91 included in the projection image 80 to derive the positional deviation amount between the projection images 80. For example, the positional deviation amount derivation unit 65 derives the positional deviation amount between the projection images 80 on the basis of the difference between the size and position of the reference object image 97 included in the pseudo-projection image 89 with a reference object and the size and position of the reference object image 91 included in the projection image 80. In a case in which it is considered that there is no positional deviation between the projection images 80, the size and position of the reference object image 97 included in the pseudo-projection image 89 with a reference object are the same as the size and position of the reference object image 91 included in the projection image 80. In addition, a method by which the positional deviation amount derivation unit 65 according to this embodiment derives the positional deviation amount between the projection images 80 on the basis of the projection images 80$_1$ to 80$_7$ and the pseudo-projection images 89$_1$ to 89$_7$ with a reference object is not limited to this embodiment.

The positional deviation amount between the projection images 80 derived by the positional deviation amount derivation unit 65 is output to the notification unit 68 and the tomographic image generation unit 71.

Similarly to the notification unit 68 (see FIG. 4) according to the first embodiment, the notification unit 68 has a function of performing notification in a case in which the positional deviation amount derived by the positional deviation amount derivation unit 65 is greater than a predetermined threshold value.

Similarly to the tomographic image generation unit 70 (see FIG. 4) according to the first embodiment, the tomographic image generation unit 71 has a function of generating a plurality of tomographic images in each of a plurality of tomographic planes on the basis of the plurality of projection images 80 acquired by the image acquisition unit 60 and the positional deviation amount derived by the positional deviation amount derivation unit 66. The tomographic image generation unit 71 outputs image data indicating the generated plurality of tomographic images to the display control unit 72.

The display control unit 72 has a function of displaying the plurality of tomographic images generated by the tomographic image generation unit 70 on the display unit 58, similarly to the display control unit 72 (see FIG. 4) according to the first embodiment.

Next, the operation of the console 12 in the tomosynthesis imaging will be described with reference to the drawings. For example, in a case in which the tomosynthesis imaging ends, the mammography apparatus 10 according to this embodiment outputs image data of a plurality of captured projection images 80 to the console 12. The console 12 stores the image data of the plurality of projection images 80 input from the mammography apparatus 10 in the storage unit 52.

After storing the image data of the plurality of projection images 80 in the storage unit 52, the console 12 performs image processing illustrated in FIG. 13. FIG. 13 is a flowchart illustrating an example of the flow of the image processing performed by the console 12 according to this embodiment. In the console 12 according to this embodiment, for example, the CPU 50A of the control unit 50 executes the image generation program 51A stored in the ROM 50B to perform the image processing illustrated as an example in FIG. 12.

In Step S100 of FIG. 13, the image acquisition unit 60 acquires a plurality of projection images 80. The image acquisition unit 60 acquires image data of a plurality of projection images from the storage unit 52 as in Step S100 (see FIG. 8) of the image processing according to the first embodiment.

Then, in Step S102, the tomographic image acquisition unit 62 acquires a plurality of tomographic images 82. As in Step S102 (see FIG. 8) of the image processing according to the first embodiment, the tomographic image acquisition unit 62 generates the plurality of tomographic images 82 corresponding to each of a plurality of tomographic planes of the breast, using the plurality of projection images 80 acquired in Step S100, and acquires the plurality of tomographic images 82.

Then, in Step S104, the pseudo-projection image generation unit 63 extracts the reference object 90 used as a reference for deriving the positional deviation amount between the projection images 80 from the plurality of tomographic images 82. As in Step S104 (see FIG. 8) of the image processing according to the first embodiment, the pseudo-projection image generation unit 63 extracts the reference object 90 which is a mammary gland from a common region of the plurality of projection images 80 on the basis of a feature amount.

Then, in Step S107, the pseudo-projection image generation unit 63 specifies the reference object region 83$_1$ of the tomographic image 82 including the reference object image 95 indicating the reference object 90. As described above, the pseudo-projection image generation unit 63 specifies the reference object region $83_1$ including the reference object image 95 in the tomographic image $82_3$ including the reference object image 95 indicating the reference object 90 extracted in Step S104.

Then, in Step S109, the pseudo-projection image generation unit 63 generates the pseudo-projection image 89 with a reference object. As described above, the pseudo-projection image generation unit 63 performs pseudo-projection on the reference object region $83_1$ of the tomographic image $82_3$ at the set irradiation position $19_V$ to generate the pseudo-projection image 89 with a reference object in the projection plane 80A of the projection image 80.

Then, in Step S113, the positional deviation amount derivation unit 65 derives the positional deviation amount between the plurality of projection images 80. As described above, the positional deviation amount derivation unit 65 derives the positional deviation amount between the projection images 80 on the basis of the reference object image 97 included in the pseudo-projection image 89 with a reference object generated in Step S109 and the reference object image 91 included in the projection image 80.

Then, in Step S114, the notification unit 68 determines whether or not the positional deviation amount between the plurality of projection images 80 is greater than a predetermined threshold value. As in Step S114 (see FIG. 8) of the image processing according to the first embodiment, the notification unit 68 determines whether or not the positional deviation amount is equal to or greater than a value at which it is preferable to perform re-imaging. In a case in which the positional deviation amount derived in Step S112 is equal to or less than the predetermined threshold value, the determination result in Step S114 is "No", and the process proceeds to Step S118. On the other hand, in a case in which the positional deviation amount derived in Step S112 is greater than the predetermined threshold value, the determination result in Step S114 is "Yes", and the process proceeds to Step S116.

In Step S116, the notification unit 68 displays a warning on the display unit 58. As in Step S116 (see FIG. 8) of the image processing according to the first embodiment, the notification unit 68 notifies the user of a warning indicating that it is preferable to perform re-imaging since the positional deviation amount is large, using the display unit 58.

Then, in Step S118, the tomographic image generation unit 70 generates a plurality of tomographic images whose positional deviation has been corrected. As in Step S118 (see FIG. 8) of the image processing according to the first embodiment, the tomographic image generation unit 70 generates a plurality of tomographic images in each of a plurality of tomographic planes on the basis of the plurality of projection images 80 acquired in Step S100 and the positional deviation amount derived in Step S113.

Then, in Step S120, the display control unit 72 displays the tomographic images generated in Step S118 on the display unit 58. In a case in which the process in Step S120 ends, the image processing illustrated in FIG. 13 ends.

As described above, the console 12 according to this embodiment processes a plurality of projection images 80 obtained by irradiating the breast with the radiation R emitted from the radiation source 29 at each of the plurality of irradiation positions 19 having different irradiation angles α. The console 12 comprises the CPU 50A. The CPU 50A acquires a plurality of projection images 80, acquires a plurality of tomographic images 82 which are generated using the plurality of projection images 80 and correspond to each of a plurality of tomographic planes of the breast, performs pseudo-projection at the set irradiation positions $19_V$ corresponding to the irradiation positions 19 of each of the plurality of projection images 80, using the tomographic image $82_3$ including the reference object image 95 used as a reference for deriving the positional deviation amount between the projection images 80 among the plurality of tomographic images 82, to generate a plurality of pseudo-projection images with a reference object which include the reference object image 97, and derives the positional deviation amount between the projection images 80 on the basis of the plurality of projection images 80 and the plurality of pseudo-projection images with a reference object.

The console 12 according to this embodiment derives the positional deviation amount between the projection images 80 using the reference object 90 which is a reference for deriving the positional deviation amount between the projection images 80. The projection image 80 has structures arranged in a direction in which the radiation R is emitted and includes a large amount of information. Therefore, the projection image 80 includes an image indicating a structure other than the reference object 90 in addition to the reference object image 91 indicating the reference object 90. In a case in which the image of another structure is superimposed on the reference object image 91, the contour of the reference object image 91 is unclear. In particular, since an image indicating a structure that is present above the reference object 90, that is, on the side close to the radiation source 29 (a structure image 93A indicating the structure 92A in FIG. 11) is superimposed on the reference object image 91, the contour of the reference object image 91 is particularly unclear.

Therefore, the console 12 according to this embodiment performs pseudo-projection at the set irradiation positions $19_V$ corresponding to the irradiation positions 19 of each of the plurality of projection images 80, using the tomographic image $82_3$ including the reference object image 95 among the plurality of tomographic images 82, to generate a plurality of pseudo-projection images 89 with a reference object which include the reference object image 97. As a result, the pseudo-projection image 89 with a reference object does not include a structure image indicating a structure which is present at a position different from that of the reference object 90, and the reference object image 97 is clearly shown. As described above, the console 12 according to this embodiment derives the positional deviation amount between the projection images 80 using the pseudo-projection images 89 with a reference object in which the positional deviation between the projected images 80 appears and which include the clear reference object image 97. Therefore, the console 12 according to this embodiment can derive the positional deviation amount between the projection images 80 with high accuracy.

In addition, the correction of the positional deviation in Step S118 may not be sufficient. In other words, in some cases, the quality of the plurality of tomographic images generated by the tomographic image generation unit 70 in Step S118 is lower than the quality of a plurality of tomographic images generated from the projection images 80 in a case in which it is considered that no positional deviation has occurred. In this case, until the positional deviation amount derived in Step S113 is equal to or less than a value at which it is considered that no positional deviation has occurred, the process may return to Step S107 after Step S118. Then, the processes in Step S107 to Step S116 may be repeated.

Further, in this embodiment, the aspect in which the pseudo-projection image generation unit 63 performs pseudo-projection on the reference object region 83₁ to generate the pseudo-projection images 89 with a reference object has been described above. However, the region on which the pseudo-projection is performed is limited to this aspect. For example, the pseudo-projection image generation unit 63 may perform pseudo-projection on the entire tomographic image 82 to generate the pseudo-projection image 89 with a reference object.

As described above, the console 12 according to each of the above-described embodiments uses the reference object 90 as a reference for deriving the positional deviation amount between the projection images 80 and derives the positional deviation amount between the projection images 80, using the component-removed images 88 or the pseudo-projection images 89 with a reference object which do not include a structure image indicating a structure other than the reference object 90. Therefore, the console 12 according to each of the above-described embodiments can derive the positional deviation amount between the projection images 80 with high accuracy.

In addition, in each of the above-described embodiments, the case in which one reference object 90 is provided has been described. However, a plurality of reference objects 90 may be provided. In this case, the console 12 may perform pseudo-projection for each of the plurality of reference objects 90. Specifically, in the first embodiment, the pseudo-projection image generation unit 64 specifies the reference object region 83₁ and the partial region 83₂ for each of the plurality of reference objects 90. Further, the pseudo-projection image generation unit 64 performs pseudo-projection for each reference object 90 using the partial region 83₂ to generate the pseudo-projection image 86 without a reference object. Further, the positional deviation amount derivation unit 66 may derive the positional deviation amount for each reference object 90, using the component-removed images 88 generated using the pseudo-projection images 86 without a reference object. Furthermore, in the second embodiment, the pseudo-projection image generation unit 63 performs pseudo-project for each of the plurality of reference objects 90 using the reference object region 83₁ to generate the pseudo-projection images 89 with a reference object. Moreover, the pseudo-projection image generation unit 63 may derive the positional deviation amount for each reference object 90 using the pseudo-projection images 89 with a reference object. In a case in which a plurality of reference objects 90 are provided as described above, for example, the positional deviation amount between the regions determined for each reference object 90 may be derived, or the positional deviation amounts for each reference object 90 may be averaged to derive the positional deviation amount of the entire projection image 80.

Furthermore, in the above-described embodiments, the aspect in which the console 12 is an example of the image processing device according to the present disclosure has been described. However, devices other than the console 12 may have the functions of the image processing device according to the present disclosure. In other words, for example, the mammography apparatus 10 or an external device other than the console 12 may have some or all of the functions of the image acquisition unit 60, the tomographic image acquisition unit 62, the pseudo-projection image generation unit 64, the positional deviation amount derivation unit 66, the notification unit 68, the tomographic image generation unit 70, and the display control unit 72. In addition, the image processing device according to the present disclosure may be configured by a plurality of devices. For example, a device other than the console 12 may have some of the functions of the image processing device.

In addition, in the above-described embodiments, the aspect in which the breast is applied as an example of the object according to the present disclosure and the mammography apparatus 10 is applied as an example of the radiography apparatus according to the present disclosure has been described. However, the object is not limited to the breast, and the radiography apparatus is not limited to the mammography apparatus. For example, the object may be the chest, the abdomen, or the like, and radiography apparatuses other than the mammography apparatus may be applied.

Further, in the above-described embodiments, for example, the following various processors can be used as the hardware structure of processing units performing various processes such as the image acquisition unit 60, the tomographic image acquisition unit 62, the pseudo-projection image generation unit 64, the positional deviation amount derivation unit 66, the notification unit 68, the tomographic image generation unit 70, and the display control unit 72, or the image acquisition unit 60, the tomographic image acquisition unit 62, the pseudo-projection image generation unit 63, the positional deviation amount derivation unit 65, the notification unit 68, the tomographic image generation unit 71, and the display control unit 72. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in each of the above-described embodiments, the aspect in which the imaging program 41 is stored (installed) in the ROM 40B in advance, and the image generation program 51 or the image generation program 51A is stored (installed) in the ROM 50B in advance has been described. However, the present disclosure is not limited thereto. Each of the imaging program 41, the image generation program 51, and the image generation program 51A may be recorded on a recording medium, such as a compact disc read only memory (CD-ROM), a digital versatile disc read only memory (DVD-ROM), or a universal serial bus (USB) memory, and then provided. Further, each of the imaging program 41, the image generation program 51, and the image generation program 51A may be downloaded from an external device through a network.

What is claimed is:

1. An image processing device that processes a plurality of projection images obtained by irradiating an object with radiation emitted from a radiation source at each of a plurality of irradiation positions having different irradiation angles, the image processing device comprising:
at least one processor,
wherein the processor acquires the plurality of projection images, acquires a plurality of tomographic images which are generated using the plurality of projection images and which correspond to each of a plurality of tomographic planes of the object, performs pseudo-projection at set irradiation positions corresponding to each of the irradiation positions of the plurality of projection images, using a group of second tomographic images other than a first tomographic image including a reference object image indicating a reference object which is used as a reference for deriving a positional deviation amount between the projection images among the plurality of tomographic images, to generate a plurality of pseudo-projection images without a reference object which do not include the reference object image, and derives the positional deviation amount between the projection images on the basis of component-removed images which include the reference object image and which are obtained by removing components of the plurality of pseudo-projection images without a reference object from the plurality of projection images.

2. The image processing device according to claim 1, wherein the processor derives the positional deviation amount on the basis of the component-removed images and the first tomographic image.

3. The image processing device according to claim 1, wherein the processor generates, as the pseudo-projection image without a reference object, a partial pseudo-projection image obtained by performing the pseudo-projection on a partial region of the group of second tomographic images which corresponds to a reference object region that is a portion including the reference object image in the first tomographic image, and removes a component of the partial pseudo-projection image from a partial image of the projection image which corresponds to the partial pseudo-projection image to generate the component-removed image.

4. The image processing device according to claim 1, wherein the processor generates images indicating differences between the plurality of projection images and the plurality of pseudo-projection images without a reference object as the component-removed images.

5. The image processing device according to claim 1, wherein the processor subtracts a pixel value of the pseudo-projection image without a reference object from a pixel value of the projection image for each corresponding pixel to generate the component-removed image.

6. The image processing device according to claim 1, wherein the processor reduces a pixel value of a pixel, which is correlated with the pseudo-projection image without a reference object, in the projection image to generate the component-removed image.

7. The image processing device according to claim 1, wherein the processor further generates a plurality of tomographic images in each of the plurality of tomographic planes on the basis of the plurality of projection images and the positional deviation amount.

8. The image processing device according to claim 1, wherein, in a case in which the positional deviation amount is greater than a predetermined threshold value, the processor performs notification.

9. The image processing device according to claim 1, wherein the processor performs the pseudo-projection on each of a plurality of reference objects using second tomographic images.

10. The image processing device according to claim 1, wherein the object is a breast, and
the reference object is a calcification or a mammary gland.

11. A radiography system comprising:
a radiation source that generates radiation;
a radiography apparatus that performs tomosynthesis imaging which irradiates an object with the radiation emitted from the radiation source at each of a plurality of irradiation positions having different irradiation angles to capture projection images of the object at each of the irradiation positions; and
the image processing device according to claim 1.

12. An image processing method that is executed by a computer and that processes a plurality of projection images obtained by irradiating an object with radiation emitted from a radiation source at each of a plurality of irradiation positions having different irradiation angles, the image processing method comprising:
acquiring the plurality of projection images;
acquiring a plurality of tomographic images which are generated using the plurality of projection images and which correspond to each of a plurality of tomographic planes of the object;
performing pseudo-projection at set irradiation positions corresponding to each of the irradiation positions of the plurality of projection images, using a group of second tomographic images other than a first tomographic image including a reference object image indicating a reference object which is used as a reference for deriving a positional deviation amount between the projection images among the plurality of tomographic images, to generate a plurality of pseudo-projection images without a reference object which do not include the reference object image; and
deriving the positional deviation amount between the projection images on the basis of component-removed images which include the reference object image and which are obtained by removing components of the plurality of pseudo-projection images without a reference object from the plurality of projection images.

13. A non-transitory computer-readable storage medium storing an image processing program that processes a plurality of projection images obtained by irradiating an object with radiation emitted from a radiation source at each of a plurality of irradiation positions having different irradiation angles, the image processing program causing a computer to execute a process comprising:
acquiring the plurality of projection images;
acquiring a plurality of tomographic images which are generated using the plurality of projection images and which correspond to each of a plurality of tomographic planes of the object;

performing pseudo-projection at set irradiation positions corresponding to each of the irradiation positions of the plurality of projection images, using a group of second tomographic images other than a first tomographic image including a reference object image indicating a reference object which is used as a reference for deriving a positional deviation amount between the projection images among the plurality of tomographic images, to generate a plurality of pseudo-projection images without a reference object which do not include the reference object image; and deriving the positional deviation amount between the projection images on the basis of component-removed images which include the reference object image and which are obtained by removing components of the plurality of pseudo-projection images without a reference object from the plurality of projection images.

* * * * *